United States Patent
Nakamura

(10) Patent No.: US 9,289,351 B2
(45) Date of Patent: Mar. 22, 2016

(54) GAS MIST PRESSURE BATHING METHOD AND GAS MIST PRESSURE BATHING SYSTEM

(71) Applicant: Shoichi Nakamura, Nagano (JP)

(72) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 154 days.

(21) Appl. No.: 14/113,751

(22) PCT Filed: Nov. 1, 2012

(86) PCT No.: PCT/JP2012/078313
§ 371 (c)(1),
(2) Date: Oct. 24, 2013

(87) PCT Pub. No.: WO2013/065779
PCT Pub. Date: May 10, 2013

(65) Prior Publication Data
US 2014/0094737 A1    Apr. 3, 2014

(30) Foreign Application Priority Data
Nov. 4, 2011 (JP) .................. 2011-242317

(51) Int. Cl.
| A61H 33/02 | (2006.01) |
| A61H 33/14 | (2006.01) |
| A61K 33/00 | (2006.01) |
| A61M 1/00 | (2006.01) |

(52) U.S. Cl.
CPC .............. *A61H 33/028* (2013.01); *A61H 33/02* (2013.01); *A61H 33/14* (2013.01); *A61K 33/00* (2013.01);
(Continued)

(58) Field of Classification Search
CPC ............. A61H 33/14; A61H 2033/14; A61H 2033/144; A61H 2203/145; A61H 2201/0157; A61H 2201/164; A61H 2201/165; A61H 2201/5082; A61H 2205/06; A61H 2205/065; A61H 2205/067; A61H 2205/106; A61H 2205/12; A61H 33/028; A61H 33/02; A61H 2033/143; A61H 2201/0207; A61K 33/00; A61K 2300/00; A61M 1/0088; A61M 1/0084; A61M 2205/3344
See application file for complete search history.

(56) References Cited

U.S. PATENT DOCUMENTS

| 8,230,853 B2 * | 7/2012 | Nakamura | ............. A61H 33/14 128/202.12 |
| 2010/0168650 A1 * | 7/2010 | Nakamura | ............ A61M 35/00 604/24 |

(Continued)

FOREIGN PATENT DOCUMENTS

JP    2009-183625 A    8/2009

*Primary Examiner* — Quynh-Nhu H Vu
(74) *Attorney, Agent, or Firm* — Manabu Kanesaka

(57) ABSTRACT

Provided are a gas mist pressure bathing method and a gas mist pressure bathing system that improve the efficiency of absorbing a gas mist from the skin and mucous membranes of a living body. The gas mist pressure bathing method is provided with a first step, a second step and a third step. The first step involves supplying a gas mist for a predetermined time to at least a first cover 51 of a living body cover member 50 having said first cover 51 and a second cover 55 positioned outside of the first cover 51, the inside of said second cover 55 being substantially sealed; covering the skin and mucous membranes of the living body; and forming a space wherein the gas mist supplied by a gas mist generating means 30 is sealed. The second step involves discharging the gas mist from the first cover 51 and/or the second cover 55. The third step involves supplying the gas mist for a predetermined time from the gas mist generating means 30 to the first cover 51 and the second cover 55, and keeping the pressure inside at least the second cover 55 in a predetermined range. The first to third steps are repeated multiple times.

17 Claims, 16 Drawing Sheets

Figure 1:
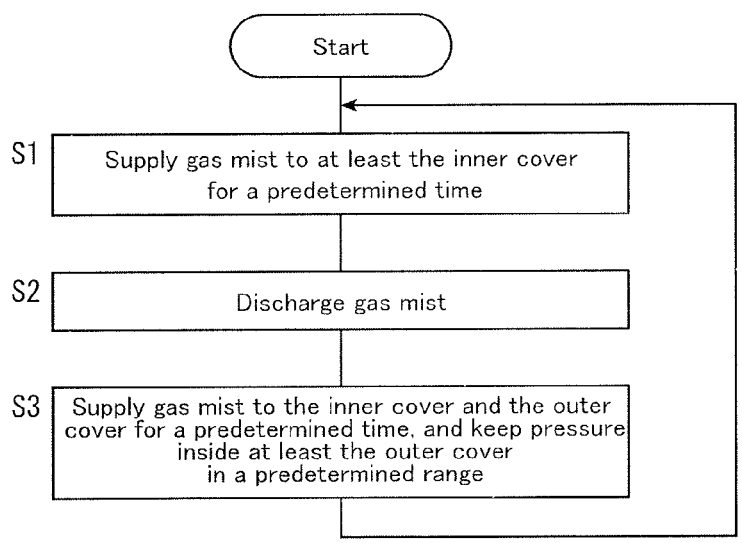

(52) U.S. Cl.
CPC ... *A61H 2033/143* (2013.01); *A61H 2201/0157* (2013.01); *A61H 2201/0207* (2013.01); *A61H 2201/164* (2013.01); *A61H 2201/165* (2013.01); *A61H 2201/5082* (2013.01); *A61H 2205/06* (2013.01); *A61H 2205/065* (2013.01); *A61H 2205/067* (2013.01); *A61H 2205/106* (2013.01); *A61H 2205/12* (2013.01); *A61M 1/0084* (2013.01); *A61M 1/0088* (2013.01)

(56) References Cited

U.S. PATENT DOCUMENTS

2010/0305497 A1* 12/2010 Tanaka ................ A61H 35/00 604/23
2011/0060259 A1* 3/2011 Nakamura .................... 601/149
2011/0208116 A1* 8/2011 Nakamura ...................... 604/24

* cited by examiner

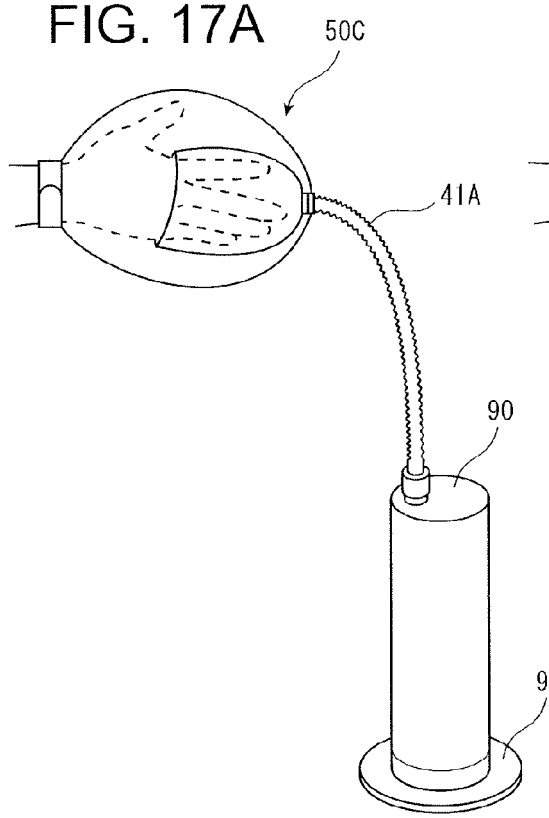
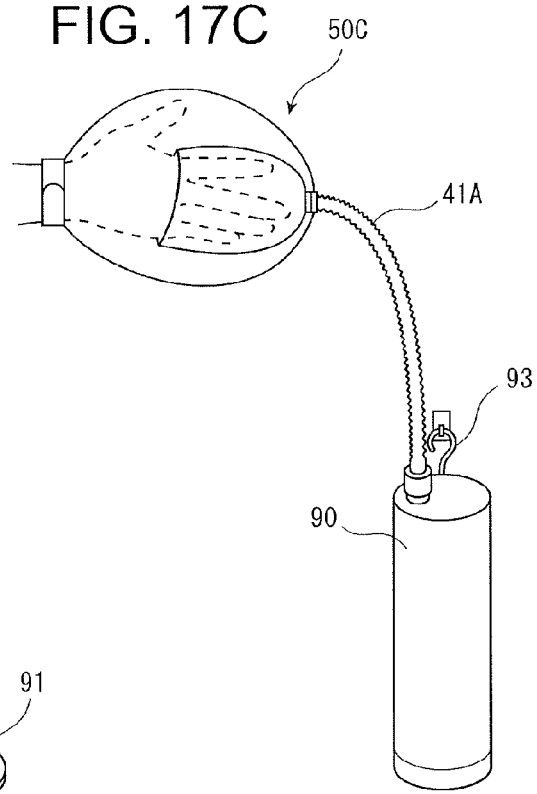
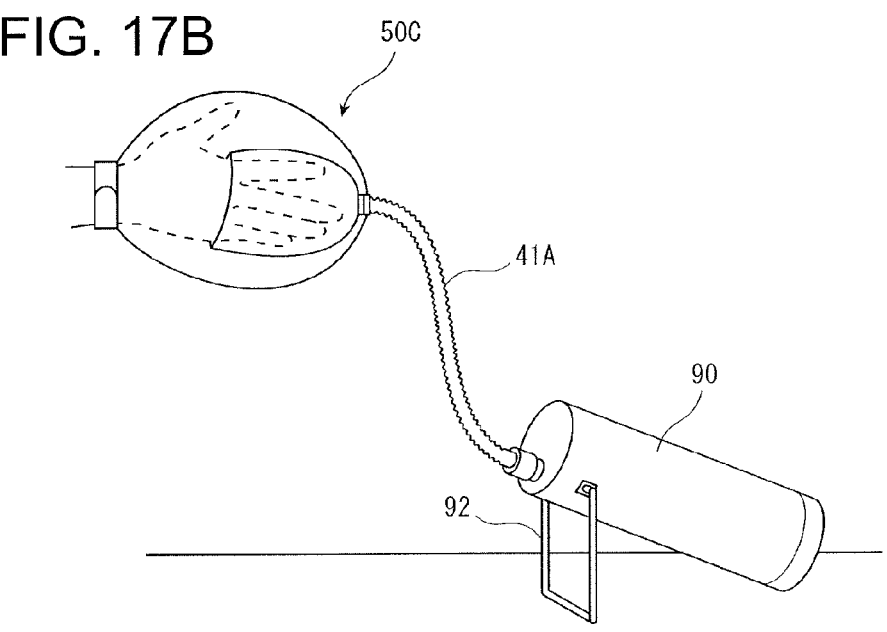

GAS MIST PRESSURE BATHING METHOD AND GAS MIST PRESSURE BATHING SYSTEM

RELATED APPLICATIONS

The present application is National Phase of International Application No. PCT/JP2012/078313 filed Nov. 1, 2012, and claims priority from Japanese Application No. 2011-242317, filed Nov. 4, 2011.

TECHNICAL FIELD

The present invention relates to a gas mist pressure bathing method and a gas mist pressure bathing system for improving absorption efficiency of gas into a skin or a mucous membrane of a living body, in which a gas mist is prepared by pulverizing liquid into micron sized mists and dissolving oxygen or carbon dioxide, or a mixed gas of oxygen, carbon dioxide, and the gas mists are caused to directly contact the skin and mucous membrane of the living body at pressure of not less than a predetermined value.

BACKGROUND OF THE INVENTION

Conventionally, it has been known that carbon dioxide (carbonic acid anhydride: $CO_2$) has two properties of being not only soluble in water (water-soluble) but also soluble in fat (fat-soluble) and, owing to such both properties, when only contacting to the skin and the mucous membrane of the living body, which are like as mixed with water and fat, carbon dioxide penetrates and expands blood vessels around the penetrated parts, and it works to improve a blood circulation. By this action of accelerating the blood circulation, it displays various physiological effects such as dropping of blood pressure, improving of metabolism or accelerating to remove pain substances or waste products. Further, it has also anti-inflammation and anti-bacterial function.

Further, recently, oxygen of high concentration has also widely been known as being effective over activity of metabolism or acceleration of blood circulation. Other than them, oxygen has effects of disinfection by or sterilization by oxidation.

An inventor of this invention has proposed up to now gas mist pressure bathing systems, in which oxygen or carbon dioxide is efficiently dissolved in the liquid to turn out a gas mist to be supplied into a living body covering member which covers the skin and mucous membrane of the living body, and caused to be absorbed into the skin and mucous membrane, so that physiological actions of their gases can be influenced effectively over to the living body.

This prior gas mist pressure bathing is performed as in following procedures.
(1) Firstly, the living body covering member is set on an optional position of the living body, and an inside of the living body covering member is sealed.
(2) Subsequently, the gas mist is generated and supplied into the inside of the living body covering member.
(3) Under maintaining prescribed conditions (pressure, temperature, moisture and others) for a predetermined time, the gas mist pressure bathing is performed.

SUMMARY OF THE INVENTION

Problems that the Invention is to Solve

However, the above mentioned prior gas mist pressure bathing system has been involved with such problems that since, due to body temperature, the inside of the member covering the skin and mucous membrane of the living body heightens the temperature, the mist therein is much evaporated, and absorption efficiency of the gas mist from the skin and mucous membrane is lowered.

In view of the above mentioned circumstances, the present invention is to provide such a gas mist pressure bathing method and a gas mist pressure bathing system, in which the living body covering member is made double, and supply of the gas mist is divided into plural turns for improving absorption efficiency of the gas mist into the skin and mucous membrane of the living body.

Means for Solving the Problems

For solving the above mentioned problems, the invention is to provide such a gas mist pressure bathing method of causing, carbon dioxide or oxygen, or a mixed gas of carbon dioxide and oxygen (called as "gas" hereafter) and a liquid which are pulverized and dissolved to turn out a mist (called as "gas mist" hereafter) at concentration of not less than a predetermined value, to contact the skin or mucous membrane of the living body, and having a first cover placed inside and a second cover placed outside of the first cover to substantially seal the inside of the first cover, and preparing (a) a first step of covering the skin and mucous membrane of the living body, and supplying the gas mist for a predetermined time into at least the first cover of the living body covering member formed with a space for sealing the gas mist supplied from the gas mist generation means and gas mixed with this gas mist, (b) a second step of discharging the gas mist from any one of the first cover and the second cover or from both, and (c) a third step of supplying the gas mist for the predetermined time into the first cover and the second cover from the gas mist generation means, and setting air pressure in at least second the cover to be within a predetermined range, and characterized by repeating the first to third steps in multiple turns.

By the way, the invention refers it as "pulverizing and dissolving" to pulverize the liquid into fine liquid drops, and cause to contact and mix with gas (carbon dioxide or oxygen, or the mixed gas of carbon dioxide and oxygen).

In the above mentioned gas mist pressure bathing method, it is also sufficient to provide a fourth step after the third step for discharging the gas mist from the inside of the living body covering member.

Further, in the first step and the third step, it is ideal to control environments in the first cover or the second cover to be within the ranges of predetermined values, based on one or plural sensors disposed within the first cover or second cover for measuring temperature, concentration of oxygen, concentration of carbon dioxide, or moisture.

Predetermined ranges of air pressure in the first cover and the second cover in the third step are desirable to be 1.01 to 2.5 air pressure.

Figure 15:
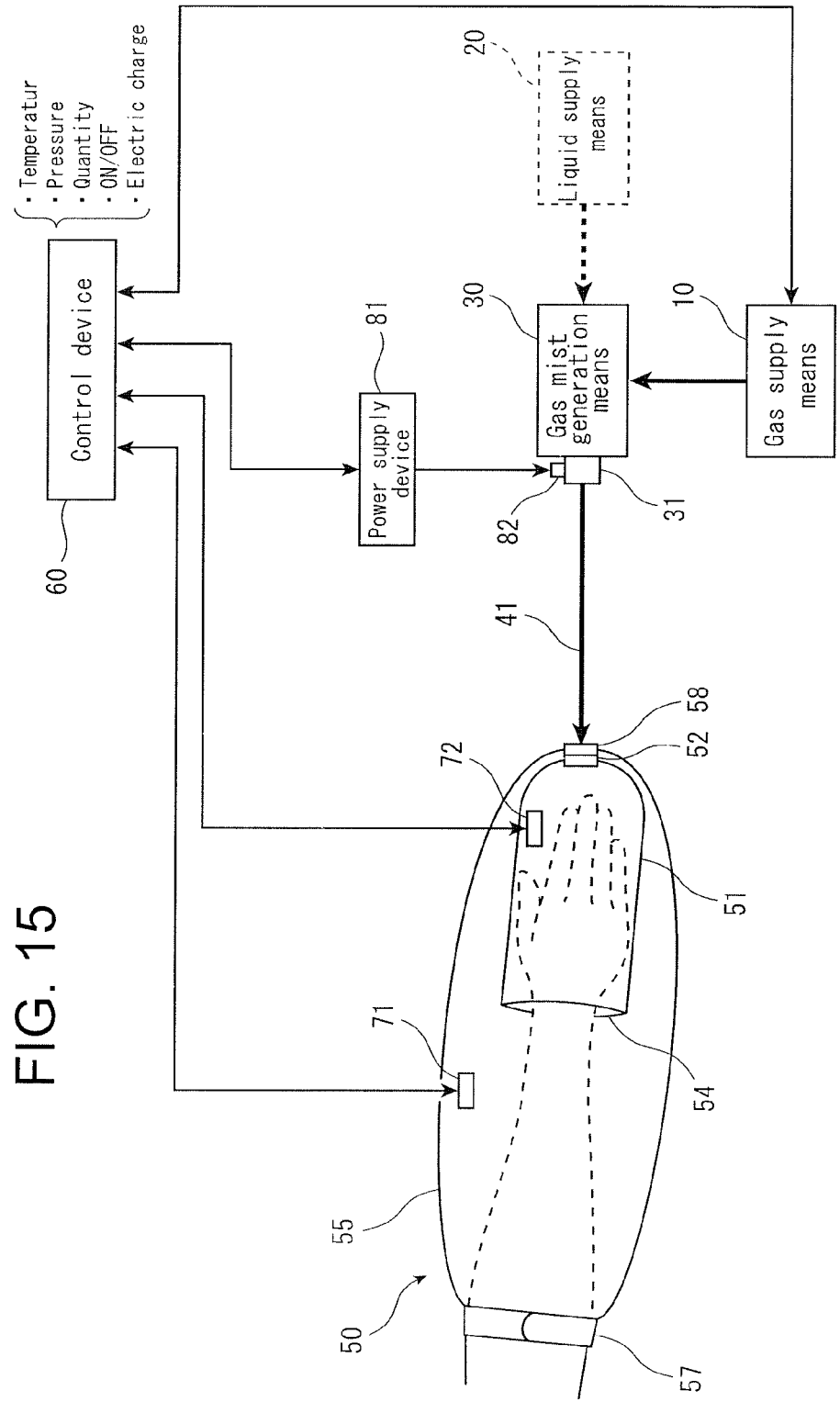
Figure 16:
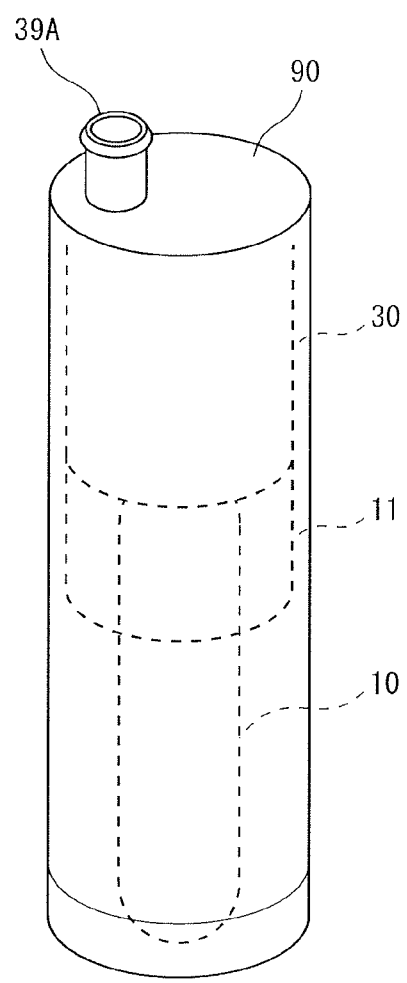

For solving the above mentioned problems, the invention is to provide such a gas mist pressure bathing system of causing carbon dioxide or oxygen, or a mixed gas of carbon dioxide and oxygen (called as "gas" hereafter) and a liquid pulverized and dissolved to turn out a mist (called as "gas mist" hereafter) at concentration of not less than a predetermined value, to contact the skin or mucous membrane of the living body, the system of the invention being furnished with a gas supply means of supplying the above mentioned gas, a gas mist generation means having a liquid storage means, generating the above mentioned gas mist with the gas supplied from the gas supply means and a liquid stored in the liquid storage, and a living body covering member which is a cover of covering the skin and mucous membrane of the living body and formed with a space for sealing inside the gas mist supplied from the gas mist generating means, characterized by furnishing a first cover placed inside and a second cover placed outside of the first cover and substantially sealing the inside of the first cover wherein a covering region of the first cover is narrower than that of the second cover, and by repeating to contact the gas mist to the covering region of the first cover, and thereafter to contact the gas mist to the covering region of the first cover and that of the second cover, thereby to improve skin-pass absorption efficiency of the gas mist.

Herein, the above mentioned gas mist pressure bathing system is preferable in that the gas mist generating means is further provided with a liquid supply means.

There may be preferably further provided manometers for measuring pressure within the first and second covers, and a control means for measuring pressure within the first and second covers on the basis of the measured values of the manometers to be within predetermined values. Further, it is suitable to control environments in the first cover or the second cover to be within predetermined values, based on one or plural sensors disposed within the first cover or second cover for measuring temperature, concentration of oxygen, concentration of carbon dioxide, or moisture.

The first cover of the living body covering member has a shape of releasing the inside depending on the opening. Otherwise, this first cover of the living body covering member has such a shape of the inside being closed.

It is preferable to further dispose any one or a plurality of the sensors within the living body covering member for measuring temperature, concentration of oxygen, concentration of carbon dioxide, or moisture.

Further, the first cover desirably includes a hand palm or a foot sole in the covering region.

The above mentioned liquid is preferably any one or plural combination of water, ionic water, ozone water, physiological salt solution, purified water, or sterilized and purified water. And it is desirable to further contain any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, citric acid, ethanol, chlorhexidine gluconate, amphoteric surface active agent, benzalkonium chloride, alkyl diamino etherglycine acetate, sodium hypochlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

Based on the control means, gas is intermittently supplied from the gas supply means into the gas mist generation means to effect interval pressurization on the living body covering member.

A size of the mist supplied from the gas mist generating means into the living body cover member is suitably not larger than 10 μm.

Further on, there may be provided an electric charge giving means for giving an electric charge to the mist supplied by the gas mist generating means. At this time, the electric charge is preferably minus.

The gas mist generating means has desirably a gas mist supply pipe for supplying the gas mist into the living body pressure bathing cover, and this gas mist supply pipe is furnished with a filter for removing liquid drops attaching to the inside of the pipe. Further, the gas mist supply pipe is composed of a cornice shaped pipe over a whole or at one part of the gas mist supply pipe. The cornice shaped pipe is formed with a groove in a shaft direction. In addition, this gas mist supply pipe is provided with a check valve.

The first cover has a gas mist supply port for receiving supply of the gas mist from the gas mist generation means, and this gas mist supply port is provided with a check valve. When the inside of the first cover is substantially sealed, the second cover is also provided with the gas mist supply port for supplying the gas mist from the gas mist generation means, and this gas mist supply port is provided with the check valve.

The control means stops gas supply from the gas supply means when pressure value within the living body covering member exceeds a predetermined value.

Effects of the Invention

Depending on the gas mist pressure bathing method and the gas mist pressure bathing system of the present invention, the skin and mucous membrane of the living body sweated and made easily absorb the gas mist is caused to contact the gas mist under an optimum condition, and effects of the gas mist pressure bathing can be heightened.

BRIEF DESCRIPTION OF THE DRAWINGS

FIG. 1 A flow chart for explaining the gas mist pressure bathing method depending on the present invention;

FIG. 2 A generally schematic view of the gas mist pressure bathing system depending on the first embodiment of the invention;

FIG. 3 A typical view in cross section (No. 1) showing the structure of the gas mist generator in the gas mist pressure bathing system of FIG. 1;

FIGS. 4A-4B A typical view in cross section (No. 2) showing the structure of the gas mist generator in the gas mist pressure bathing system of FIG. 1;

FIG. 5 A typical view in cross section (No. 3) showing the structure of the gas mist generator in the gas mist pressure bathing system of FIG. 1;

FIG. 6 A perspective view, partially in section, showing the gas mist generator shown in FIG. 5;

FIG. 7 A typical view in cross section (No. 4) showing one example of the structure of the gas mist generator in the gas mist pressure bathing system of FIG. 1;

FIG. 8 A typical view showing the example of the gas mist supply pipe connecting the gas mist generator to the living body pressure bathing cover of the invention;

FIG. 9 A perspective view in cross section of the gas mist supply pipe shown in FIG. 8;

FIG. 10 A flow chart for explaining the gas mist pressure bathing method depending on the first embodiment of the invention;

FIGS. 11A-11D Typical views showing examples of shapes of the living body pressure bathing covers in the gas mist pressure bathing system depending on the first embodiment of the invention;

FIG. 12 A typical view (No. 1) showing an example of the shape of the living body pressure bathing cover in the gas mist pressure bathing system depending on the second embodiment of the invention;

FIG. 13 A flow chart for explaining the gas mist pressure bathing method depending on the second embodiment of the invention;

FIGS. 14A-14D Typical views (No. 2) showing examples of shapes of the living body pressure bathing covers in the gas mist pressure bathing system depending on the second embodiment of the invention;

FIG. 15 A generally schematic view of the gas mist pressure bathing system depending on the third embodiment of the invention;

FIG. 16 A typical view showing a general appearance when housing the gas supply means and the gas mist generator of the invention in a case; and FIGS. 17A-17C Typical views showing examples of using the cases shown in FIG. 16.

EMBODIMENTS FOR PRACTICING THE INVENTION

In the following description, explanations will be made to embodiments of this invention, referring to the attached drawings.

The invention makes use of temperature-rise within the living body covering member owing to body-temperature, which has been one of prior problems as having mentioned above for taking effectively gas mist pressure bathing. That is, the invention makes a double structure having an inner cover and an outer cover of the living body covering member sealed with the gas mist, in which the inner cover is used for causing the gas mist to locally contact the skin or the mucous membrane of the living body, and the outer cover is used as a pressure controlling cover for absorbing the gas mist.

For the living body to absorb the gas mist from the skin or the mucous membrane, three routes are mainly present. One of them is called as "pore-pass quality", which is such a route absorbed from pores existing in a cuticle into a cortical layer through follicular or sebaceous gland. A second is called as "cuticle-pass quality", which is such a route gradually penetrating into a lower layer from a stratum corneum of the cuticle. A third is called as "sweat gland-pass quality" from the sweat gland existing in the cuticle into the cortical layer.

In a human body, many sweat glands exist from skin deep cortical layers over subcutaneous tissues. The sweat glands are divided into small sweat glands (eccrine gland) and large sweat glands (apocrine gland), and in particular, the small sweat glands are many in the hand palm and the foot sole, and are told as existing 2000000 to 5000000 pieces.

The sweat gland mainly works to secrete sweat for keeping the body temperature constant, but as said above, also largely concerns cutaneous absorption of materials. When skin temperature rises, the sweat is secreted to humidify the skin. Then, a protein combination of the stratum corneum is loosened to make subcutaneous penetration easy, so that the sweat glands or the pores are concurrently widened, blood penetration is accelerated thereby, and the gas mist absorption is carried out very efficiently.

Therefore, the invention composes the living body covering member with double covers of the inner cover (first cover) and the outer cover (second cover), and attaches to the living body. The region of the living body for attaching the inner cover includes parts having many sweat glands existing in the palms or the soles. The outer cover attaches to substantially seal the whole of the inner cover.

Showing in FIG. 1, as a first step (Step S1), the gas mist is supplied into at least the inner cover for a predetermined time. Subsequently, as a second step (Step S2), the gas mist is discharged from any one or both of the inner cover and the outer cover, and further, as a third step (Step S3), the gas mist is supplied into the inner cover and the outer cover for the predetermined time, and the air pressure within at least the second cover is brought to be in the predetermined range. By repeating these steps over plural turns, sweating by temperature rise within the cover as well as skin-pass absorption as checking the gas mist evaporation are repeated, so that the gas mist is caused to be absorbed at high efficiency.

That is, by utilizing rise of temperature within the living body covering member owing to the body temperature together with lapse time, the sweat gland at the covered range of the living body is made opened to sweat out. When the pressure value in the living body covering member rises under a condition of sweating at the covered range, the skin-pass absorption is much smoothed. On the other hand, since the gas mist is gasified in company with temperature rising within the living body covering member, the step of supplying the gas mist is repeated, and the inside of the living body covering member is filled with the gas mist of high concentration. The sweat gland is thereby opened and the covered range under the sweating condition is contacted with the gas mist of the high concentration, so that skin-pass absorption of the gas mist is enabled at high efficiency.

In the following, more concrete explanations will be made to practicing examples.

First Embodiment

Figure 2:
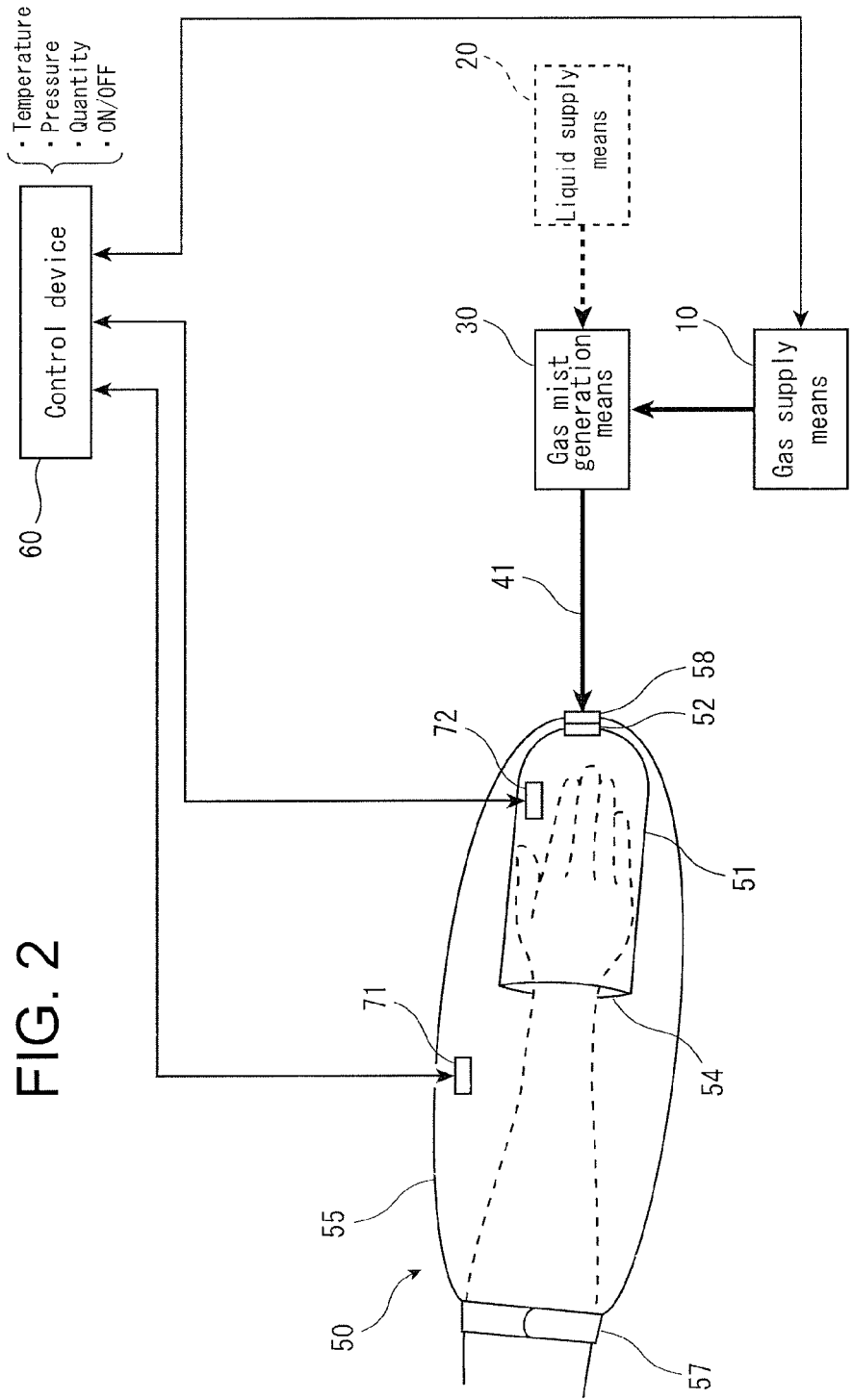

FIG. 2 is the generally schematic view of the gas mist pressure bathing system depending on the first embodiment of the invention. Showing in FIG. 2, the gas mist pressure bathing system of this embodiment is composed of a gas supply means 10 for supplying oxygen, carbon dioxide, or the mixed gas of oxygen and carbon dioxide (called as merely "gas" hereafter), a gas mist generator 30 as a gas mist generation means, a living body pressure bathing cover 50 as a living body covering member for sealing inside the supplied gas mist, and a control device 60 as a control means.

The gas supply means 10 supplies gas to a later mentioned gas mist generator 30. For example, a gas bomb of a cartridge system, a cassette bomb or a gas container of high pressure for official uses are also sufficient. The gas supply means 10 is desirably attached with a regulator for adjusting gas pressure, though not showing.

The gas mist generator 30 is a device which generates the gas mist with gas supplied from the gas supply means 10 and liquid, and supplies it to the living body pressure bathing cover 50, and as showing in FIGS. 3 to 7, various types may be employed. One type of the gas mist generator 30 stores liquid inside to generate the gas mist, while another type receives supply of liquid from an exterior to generate the gas mist. In the case of the gas mist generator 30 receiving supply of liquid from the exterior, it is necessary to furnish a liquid supply means 20 as showing with a broken line in FIG. 2.

Figure 3:
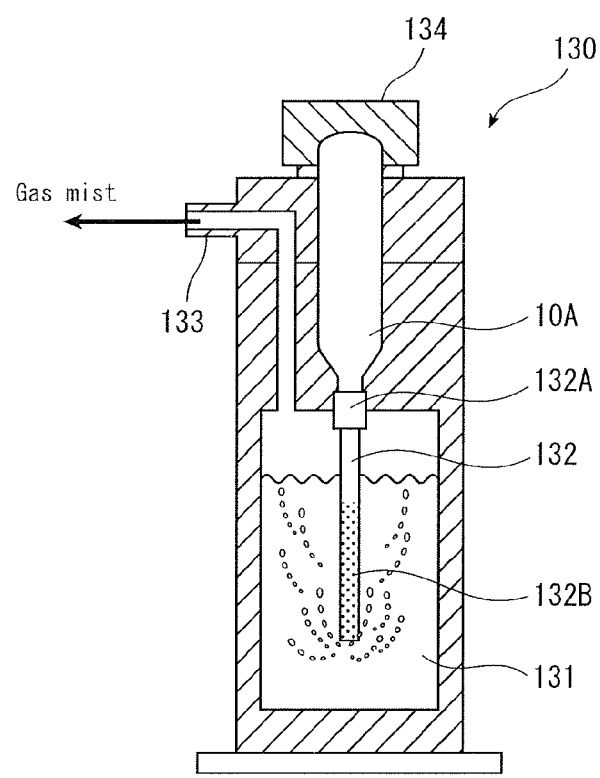

FIG. 3 is the typical view of the gas mist generator 130 which generates the gas mist by changing liquid into minute liquid drops in a manner of jetting gas of high pressure from the gas supply means 10 into the liquid. This gas mist generator 130 has a liquid storage 131 of storing the liquid, a gas introduction part 132 of introducing gas into the inside of the liquid storage 131 and releasing it, and a gas mist discharge port 133 for discharging the gas mist generated in the liquid storage 131.

Incidentally, it is shown that the gas mist generator 130 is built-in with a small typed gas bomb 10A of a cartridge system as the gas supply means 10, and another gas supply means 10 is also sufficient, or may be such a structure not built-in but furnished outside. Besides, here is shown an example of previously storing the liquid in the liquid storage 131, but such a structure is also enough of supplying the liquid each time from the liquid supply means 20 (refer to FIG. 2).

A gas introduction part 132 is an almost tubular member having, at its upper end, a connection part 132A to the gas supply means 10 and plural fine pores 132B for discharging gas nearly at a lower end. The gas from the gas supply means 10 is supplied from the connection part 132A and is released into the liquid from the fine pores 132B.

For using the gas mist generator 130, at first, under a condition of storing the liquid in the liquid storage 131, the gas is released into the liquid from the gas supply means 10 via the gas introduction part 132. Herein, the gas bomb 10A is set in the gas mist generator 130, and when the cap 134 is screwed, the gas bomb 10A is pressed downward by the cap 134 and is urged to a connection part 132 A of the gas introduction part 132. Since the connection part 132A is provided with a mechanism of opening the gas bomb 10A, though not showing, when the cap 134 is screwed up, the gas bomb 10A is pushed down and opened, and the gas is forcibly spouted from the fine pores 132B into the liquid. By the way, such a structure will be allowed not to discharge the gas until a predetermined pressure or more by furnishing a spring or the like to the connection part 132A.

Discharging the gas at high pressure into the liquid stored in the liquid storage 131, the gas mist happens at a time when occurring bubbles are burst. The generated gas mist spreads over inside the liquid storage 131, and is discharged from the gas mist discharge port 133 owing to gas convection. The discharged gas mist is supplied into the living body pressure bathing cover 50 via a later mentioned gas mist supply pipe 41.

Figure 4A:
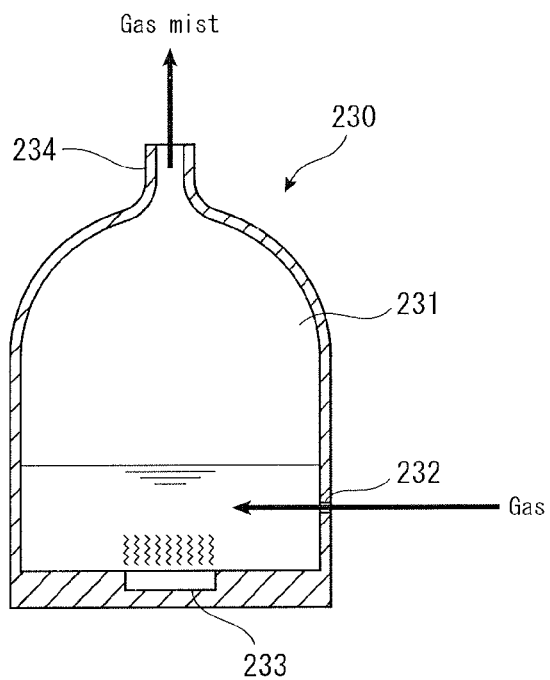

Next explanation will be made to a gas mist generator 230 using supersonic wave, referring to FIGS. 4A and 4B. As showing in FIG. 4A, the gas mist 230 has a liquid storage 231 of storing the liquid, a gas supply port 232 of supplying the gas from the gas supply means 10 into the liquid stored in the liquid storage 231, a supersonic vibrator 233 of generating the gas mist by adding supersonic vibration to the liquid stored in the liquid storage 231, and a gas mist discharge port 234 of discharging the generated gas mist.

Incidentally, here is shown an example of having previously stored the liquid in the liquid storage 231, but such a structure is also sufficient of supplying each time the liquid from the liquid supply means 20 (refer to FIG. 2).

For using the gas mist generator 230, at first, the gas from the gas supply means 10 is released into the liquid stored in the liquid storage 231 via the gas supply port 232 to dissolve the gas in the liquid. In addition, supersonic vibration is given to the liquid by a supersonic vibrator 233.

The supersonic vibrator 233 has a piezoelectric element, and is so disposed that its plane of vibration is exposed to the liquid storage 231 so that it directly contacts the liquid, or closely attaches the bottom of the liquid storage 231. When actuating the piezoelectric element, supersonic vibration is transmitted to the liquid, and concurrently minute droplets happen from a liquid surface, so that those turn out the gas mist containing gas. The generated gas mist spreads over within the liquid storage 231, and is discharged from the gas mist discharge port 133 owing to gas convection. The discharged gas mist is supplied into the living body pressure bathing cover 50 via a later mentioned gas mist supply pipe 41.

Figure 4B:
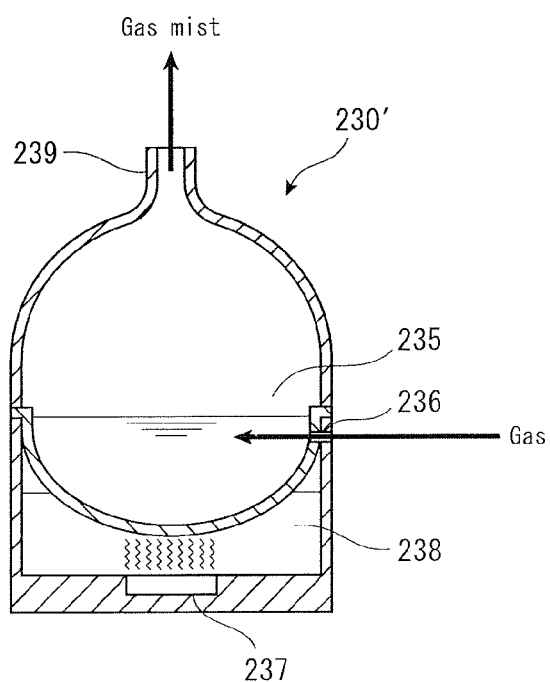

On the other hand, as a gas mist generator 230' shown in FIG. 4B, it is allowed that vibration of the supersonic vibrator is not directly but indirectly given to the liquid via a transmission layer of the supersonic vibration. The gas mist generator 230' is the storage of storing the liquid, and at the same time, has the liquid storage 235 as a gas mist generation cistern of generating the gas mist, a gas supply port 236 for supplying the gas from the gas supply means 10 into the liquid stored in a liquid storage 235, the supersonic vibrator 237 of adding supersonic vibration to the liquid stored in the liquid storage 235 for generating the gas mist, a vibration transmitting cistern 238 storing the liquid in the liquid storage 235 to be transmitted with supersonic vibration, and a gas mist discharge port 239 for discharging the generated gas mist.

By the way, here is shown an example of having previously stored the liquid in the liquid storage 235, but such a structure is also sufficient of supplying each time the liquid from the liquid supply means 20 (refer to FIG. 2).

The bottom of the gas mist generation cistern composing the liquid storage 235 is, as shown in FIG. 4B, disposed taking a space not to contact the bottom of the vibration transmitting cistern 238. The gas mist generation cistern is preferably formed with a plastic of thickness being about 0.2 to 0.3 mm for effectively transferring supersonic vibration. The vibration transmitting cistern 238 is filled with the liquid (suitably, water) for transferring vibration to the liquid storage 235.

For using the gas mist generator 230', at first, the gas from the gas supply means 10 is released into the liquid stored in the liquid storage 235 via the gas supply port 236 to dissolve the gas in the liquid. In addition, supersonic vibration is given to the liquid in the liquid storage 235 via the liquid in the vibration transmitting cistern 238 by a supersonic vibrator 237.

The supersonic vibrator 237 has the piezoelectric element, and is disposed in such manners that that its plane of vibration is exposed to the vibration transmitting cistern 238 so that it directly contacts the liquid, or closely attaches the bottom of the liquid storage 238. When actuating the piezoelectric element, supersonic vibration is transmitted to the liquid in the liquid storage 235 via the liquid in the vibration transmitting cistern 238, and concurrently minute droplets occur from the liquid surface, so that those turn out the gas mist containing gas. The generated gas mist spreads over within the liquid storage 235, and is discharged from the gas mist discharge port 239 owing to the gas convection. The discharged gas mist is supplied into the living body pressure bathing cover 50 via a later mentioned gas mist supply pipe 41.

Next explanation will be made to a gas mist generator for generating the gas mist by a system as spraying owing to flowing of high speed of gas supplied from the gas supply means 10.

Figure 5:
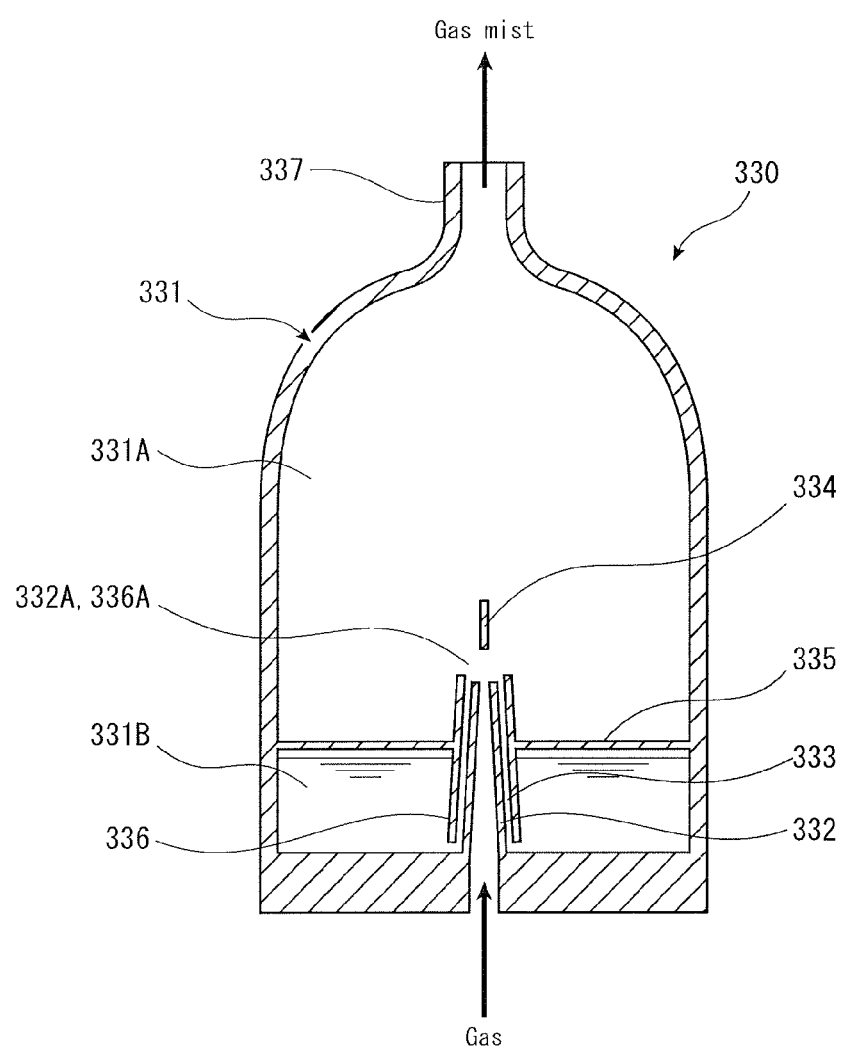

FIG. 5 shows a basic example. A gas mist generator 330 has a storage 331 (a gas mist storage 331A and a liquid storage 331B), a nozzle 332 of discharging gas supplied from the gas supply means 10 from its front end open, a liquid suction pipe 333 of sucking up the liquid stored in the liquid storage 331B till the front end of the nozzle 332, a baffle (a collision member) 334 furnished in position to the front end of the nozzle 332, and a gas mist discharge port 337 for discharging the generated gas mist.

Figure 6:
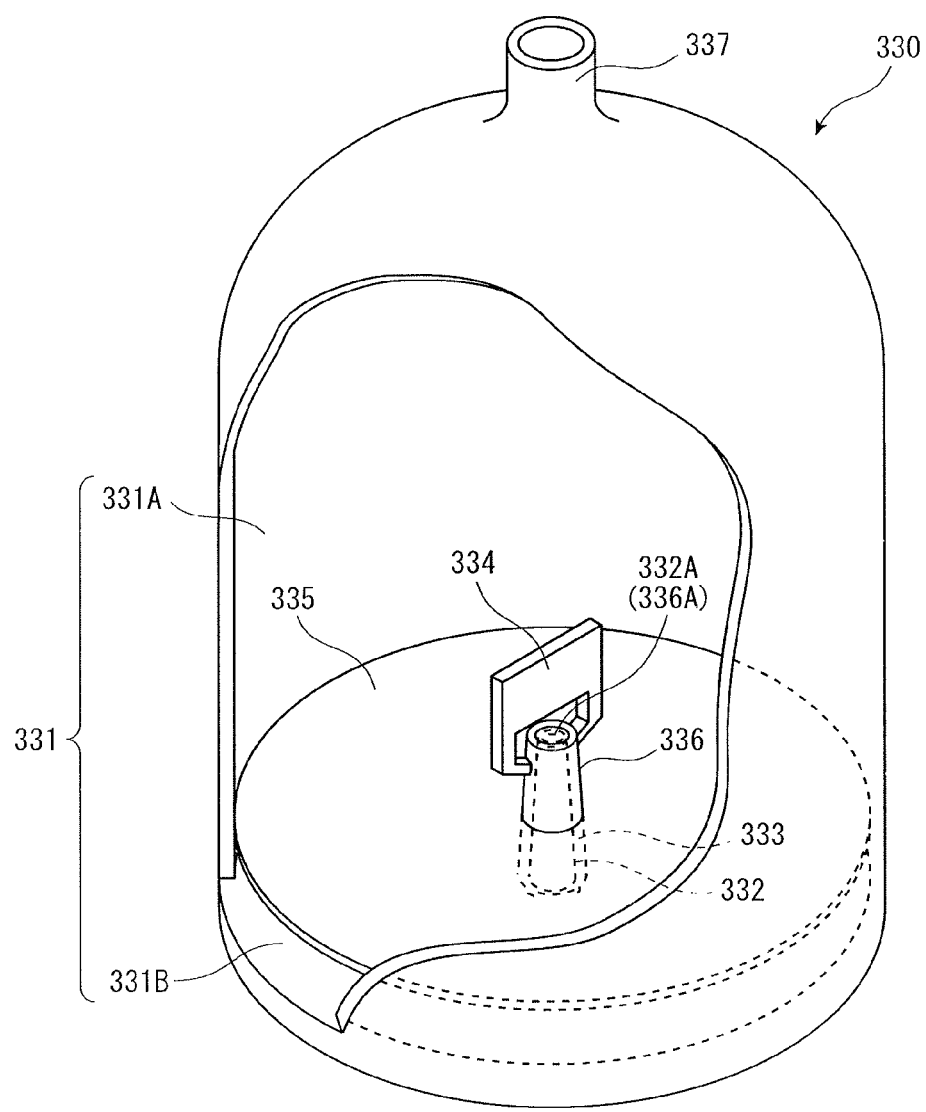

The storage 331 is, as showing in FIG. 6, divided by a shield plate 335 into an upper gas mist storage 331A and a tower liquid storage 331B. At the center of a bottom of the storage 331, a nozzle 332 is equipped. The nozzle 332 is formed as a substantially conical tube from the bottom of the storage 331 toward the upper part. Its base is connected to the gas supply means 10 at the outside of the device, while its front end projects to the side of the gas mist storage 331A, so that gas can be discharged from a front end open 332A.

Incidentally, here is shown an example of having previously been stored the liquid in the liquid storage 331B, but such a structure is also sufficient of supplying each time the liquid from the liquid supply means (refer to FIG. 2).

The liquid suction pipe 333 is formed between the nozzle 332 and a liquid suction pipe-forming member 336 shaped in the almost circular cone being larger by one turn than the nozzle 332. That is, by positioning the liquid suction pipe-forming member 336 as covering over the nozzle 332, the liquid suction pipe 333 is defined between the outer circumference of the nozzle 332 and the inner circumference of the liquid suction pipe-forming member 336. Further, a space is defined between the base end of the liquid suction pipe-forming member 336 and the bottom of the liquid storage 331B. From this space, the liquid stored in the liquid storage 331B is sucked up by the liquid suction pipe 333. In addition, a front end 336A of the liquid suction pipe-forming member 336 opens nearly a front end open 332A of the nozzle 332, and the liquid sucked up in the liquid suction pipe 333 collides with the gas flow discharged from the nozzle 332.

The baffle 334 is a member disposed at such a position opposite to the front end open 332A of the nozzle 332 and the front end 336A of the liquid suction pipe-forming member 336, and herein, the baffle 334 is connected to the liquid suction pipe-forming member 336. Otherwise, such a structure is sufficient, of communicating with the shield plate 335 or storage 331. By the way, the liquid suction pipe-forming member 336 is illustrated as communicating with the shield plate 335 at an almost central part in the vertical direction, and the shield plate 335 also communicates with the inside of the storage 331 at the outer circumference, but those are sufficient to other positions or may be independent parts not connected.

When generating the gas mist with the gas mist generator 330 as mentioned above, the gas is supplied from the gas supply means 10 to the nozzle 332 under a condition of having previously stored the liquid in the liquid storage 331B. Then, since the nozzle 332 is reduced in diameter toward the front end, the gas is spouted by increasing the flowing speed. The liquid is sucked up in the liquid suction pipe 333 due to negative pressure generated by air stream at this time, and is blown up by gas flowing in the vicinity of the front end open of the nozzle 332 and is collided against the lower end of the baffle 334. By this collision, the liquid is pulverized, mixed with gas, dissolved, and thus, the gas mist is generated. The generated gas mist is spread within the gas mist storage 331A, and is discharged from the gas mist discharge port 337, following the gas convection. The discharged gas mist is supplied into the living body pressure bathing cover 50 via a later mentioned gas mist supply pipe 41.

Further, explanation will be made to the gas mist generator of generating the gas mist by using a fluid nozzle.

Figure 7:
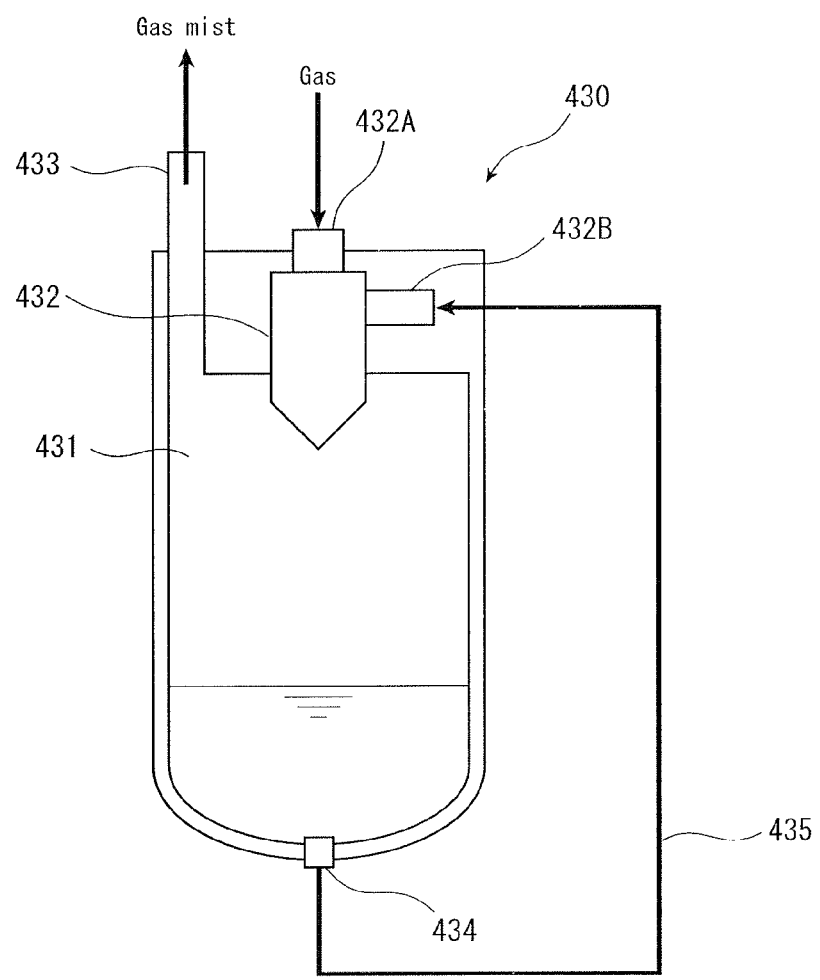

As showing in FIG. 7, a gas mist generator 430 has a liquid storage 431 of storing the liquid, a liquid nozzle 432 of generating the gas mist with the gas supplied from the gas supply means 10 and the liquid, and a gas mist discharge port 433 of discharging the gas mist generated by the liquid nozzle 432.

In the bottom part of the liquid storage 431, a liquid discharge part 434 is furnished, and is connected with a liquid circulation path 435.

The fluid nozzle 432 is a binary nozzle which generates the gas mist by utilizing high speed of gas supplied from the gas supply means 10. The fluid nozzle 432 has a gas supply port 432A connected with the gas supply means 10 and a liquid supply port 432B which connected through a liquid discharge part 434 and liquid circulation path 435.

When supplying the gas to the fluid nozzle 432 from the gas supply means 10 under a condition of having previously stored the liquid in the liquid storage 431, the inside of the liquid storage 431 is effected with high pressure, and the liquid is sent from the liquid discharge part 434 into the liquid circulation path 435. The liquid having reached a liquid supply port 432B of the fluid nozzle 432 from a liquid circulation path 435, is changed into the gas mist by the fluid nozzle 432, and sprayed into the liquid storage 431. The gas mist sprayed to the liquid storage 431 is supplied into the living body pressure bathing cover 50 from the gas mist discharge port 433 via the gas mist supply pipe 41, and one part of the gas mist melts into the liquid staying in the liquid storage 431. By melting the gas mist, the gas is dissolved in the liquid, and this liquid is further sent to the liquid circulation path 435 and is sprayed from the liquid nozzle 432, and this circulation is repeated. As a result, while the liquid repeats such a circulation, the dissolving concentration of gas becomes higher, and the gas mist dissolving gas at high concentration can be generated.

It is sufficient to dispose a liquid pressurizer such as a pump in the liquid circulation path 435 for circulating the liquid efficiently. Incidentally, here is shown the example of having previously stored the liquid in the liquid storage 431, but such a structure is also sufficient of supplying each time the liquid from the liquid supply means (refer to FIG. 2) into the liquid supply port 432B of the fluid nozzle 432 without furnishing the liquid circulation path 435.

Herein, as the liquid stored or supplied in the gas mist generator 30, it is preferable to employ water, ionic water, ozone water physiological salt solution, purified water or sterilized and purified water. Further, these liquids are sufficient to contain medicines useful to users' diseases or symptom. As the medicines, for example, listed are anti-allergic agent, anti-inflammatory agent, anti-febrile agent, anti-fungus agent, anti-influenza virus agent, influenza vaccine, steroid agent, anti-cancer agent, or anti-hypertensive agent, cosmetic, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic agent moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, ant-inflammatory agent, pain-killing, anesthetic, and immunity. Otherwise, the liquid may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate. In addition, carbonate spring of high concentration may be added (examples of organic components are sulfate, carbonate, or sodium dichloroiso-cyanurate).

Figure 8:
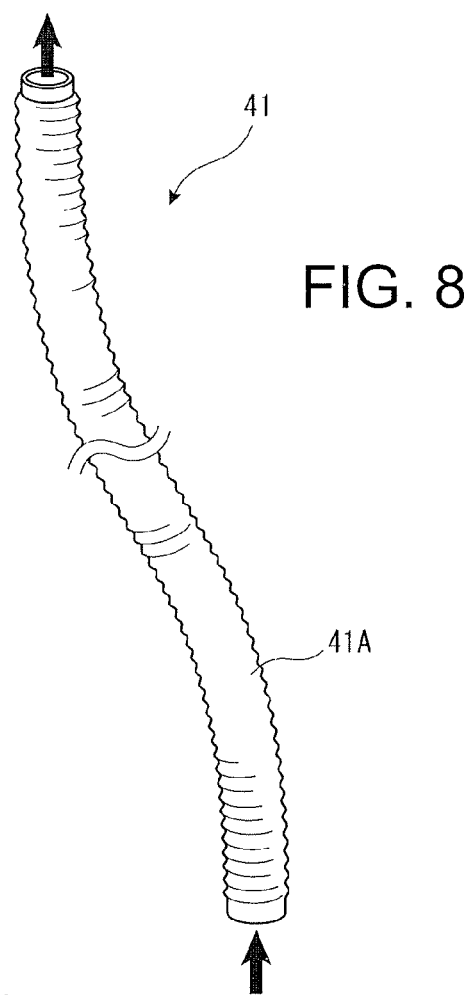
Figure 9:
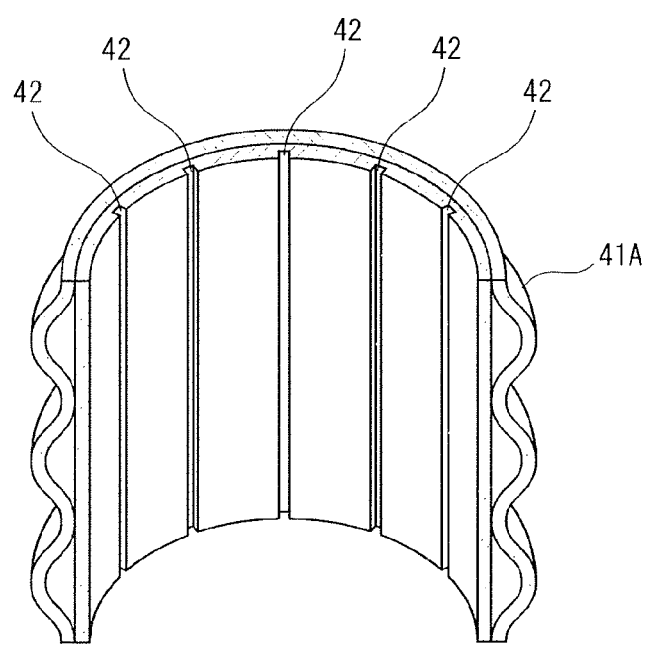

The gas mist supply pipe 41 (refer to FIG. 2) of supplying the gas mist discharged from the gas mist generator 30 into the living organist pressure bathing cover 50, is desirably composed wholly or partially with a soft and cornice shaped pipe 41A of large diameter as shown in FIG. 8, and this is freely bent or expanded and contracted so that a user's action is not limited. In addition, as shown in FIG. 9, the cornice shaped pipe 41A is formed inside with grooves 42 in an axial direction of the pipe. By thus forming inside the grooves 42 of the pipe 41A, when the gas mist flowing in the gas mist supply pipe 41 becomes liquefied, liquid drops can be easily collected and recovered. FIG. 9 illustrates the inside of the cornice shaped pipe 41A is smooth, but may be formed to be cornice shape as the outside. Also in such a case, by forming the grooves 42, the liquefied gas mist is recovered.

The gas mist supply pipe 41 is provided inside with a check valve to avoid back flows of the gas mist. Further, though not showing, the gas mist supply pipe 41 is preferably provided with a droplet removing filter to remove extra droplets attaching to the inside of the pipe.

The living body pressure bathing cover 50 is such a cover which covers the skin and mucous membrane of the living body (in FIG. 2, as the example, a forearm of the human body), forming a space for sealing inside the gas mist. The living body pressure bathing cover 50 is composed of a first cover (an inner cover) 51 positioned inside and a second cover (an outer cover) 55 positioned outside to cover the whole of the first cover 51 and enable to substantially seal. The living body pressure bathing cover 50 is preferably composed of pressure resistant, non-air permeable and non-moisture permeable materials, for example, a natural rubber, silicone rubber, polyethylene, polypropylene, polyvinylidene, poly-styrene, polyvinylacetate, polyvinyl chloride, polyamide resin, polytetrafluoroethylene, and the like.

The inner cover 51 is a substantially bag-shaped cover for covering locally regions being high at absorption rate of the gas mist, and at the same time, functions as a heat insulating cover. That is, after temperature rises within the living body pressure bathing cover member 50 as time passes, the gas mist generated at room temperature and relatively low temperature is supplied, and the inner cover 51 is suitably composed with a heat insulating material not to soon rise. By attaching this inner cover 51, it is possible to avoid evaporation of the gas mist supplied during taking the gas mist pressure bathing. The inner cover 51 is attached to such regions of especially absorbing the gas mist, having many sweat glands and easily sweating as the palm or sole.

The inner cover 51 has a supply port 52 connected to the gas mist supply pipe 41 for introducing the gas mist into the inside thereof. This supply port 52 is has a check valve for preventing back flows of the gas mist, though not showing. An end of the inner cover 51 is here an opening 54. Accordingly, the gas mist supplied in the inner cover 51 is also supplied into the outer cover 55 through the opening 54.

The outer cover 55 is larger than the inner cover 51, can cover the skin and mucous membrane of the living body and wholly the inner cover 51, and is formed almost as a bag. At an opening of the outer cover 55, a stopper 57 is furnished for enabling to attach to and detach from the living body, and for avoiding leaking the gas mist sealed inside. The stopper 57 is suitably composed of, e.g., a face fastener of stretching property, or may have a string, rubber or their combination. Further, since the outer cover 55 necessitates a sealing property, the inside of the stopper 57 may be disposed with a material adhesive to the skin of the living body. This adhesive material is preferably, for example, a visco-elastic gel made of polyurethane or silicone rubber. Further this adhesive material is detachably used and exchangeable each time, if viscosity becomes weak.

Further, the outer cover 55 is provided with a connection part 58 for connecting a supply port 52 of the inner cover 51 and for connecting the inner cover 51 and the gas mist supply pipe 41 as closing the inside of the outer cover 55. Not showing, the outer cover 55 is suitably provided with a gas mist discharge port for discharging the gas mist from the inside of the cover, or with a valve for controlling pressure of the inside of the cover. Pressure within the cover may be controlled manually, but automatic performance is desirable by a control device 60 together with supply control of the gas mist based on measuring values of a later mentioned manometer 71. A safety valve (escape valve) is desirably furnished for automatically opening the valve when the inside of the outer cover 55 comes above a fixed pressure value.

There has been shown such a structure, as an example, having the connection part 58 for connecting the supply port 52 of the inner cover 51, but if being able to supply the gas mist to the inner cover 51 as sealing the inside of the outer cover 55, any forms may be applied.

The outer cover 55 is installed with the manometer 71 for measuring pressure of the inside thereof. The control device 60 controls generation and supply of the gas mist, based on the measured values of the manometer 71 for keeping the pressure value within the cuter cover 55 to be not less than 1 air pressure (more preferably, 1.01 to 2.5 air pressure). For example, supply of gas from the gas supply means 10 is adjusted or stopped, otherwise, the gas mist is discharged from the inner cover 51 or from the outer cover 55. By the way, since the present embodiment uses the living body pressure bathing cover 50 under the condition where the inner cover 51 is released by the opening 54, the manometer 71 is enough with one provided within the outer cover 55. Further, as showing in FIG. 2, a temperature gage 72 may be installed for measuring temperatures within the inner cover 51 or the outer cover 55 (herein, within the inner cover 51). The control device 60 turns ON-OFF of supplying the gas mist from measuring values of the temperature gage 72.

As to others, there may be installed sensors within the living body pressure bathing cover 50 for measuring concentration of oxygen, concentration of carbon dioxide or moisture for controlling environments in the covers to be within respectively predetermined values by the control device 60.

The control device 60 is composed of a computer having CPU, memory and display. Various kinds of controls are performed such as control or ON-OFF switch of gas pressure supplied from the gas supply means 10, or ON-OFF switch of supplying the gas mist for carrying out the gas mist pressure bathing under an optimum condition. In particular, from the measuring values of the sensors of the manometer 71 or the temperature gage 72 installed in the living body pressure bathing cover 50, the respective means are controlled to keep the optimum condition within the living body pressure bathing cover 50 for taking the gas mist pressure bathing. When the pressure value in the living body pressure bathing cover 50 is higher than the predetermined value, such a structure of the system is suitably built to stop the gas supply of the gas supply means 10 by the control device 60. Incidentally, the above mentioned controls may be manual without using the control device 60.

Figure 10:
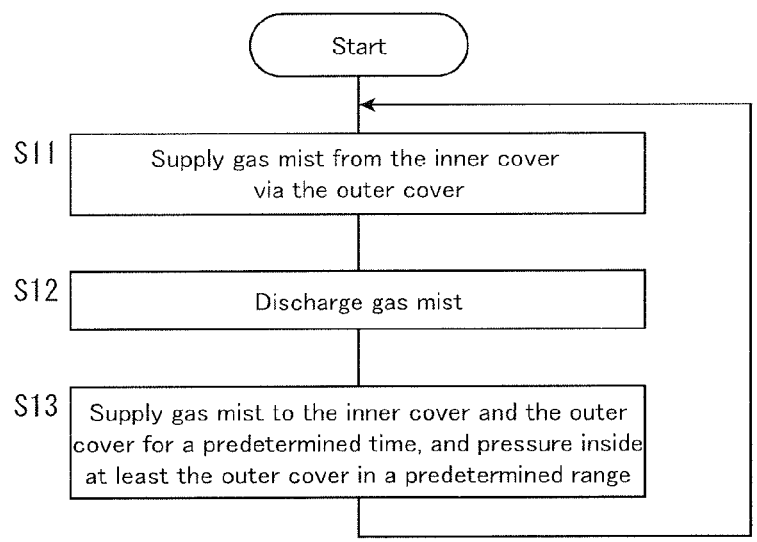

Following explanations will be made with FIG. 10 to the gas mist pressure bathing method using the gas mist pressure bathing system of the above mentioned embodiment.

At first, as a preparatory step, the gas mist generator 30 is brought to under a usable condition as manners of opening the sealed gas mist generator 30 and connecting to the gas supply means 10. As to the living body pressure bathing cover 50, the inner cover 51 is attached to an optional part of the living body, and subsequently, the outer cover 55 is attached to cover the whole of the inner cover 51 for securing to the living body to substantially seal the inside.

Next, gas supply is started from the gas supply means 10 into the gas mist generator 30 to generate the gas mist and supply it into the inner cover 51 for a predetermined time (Step S11). In the present embodiment, the gas mist is also supplied into the outer cover 55 via the inner cover 51. By supplying the gas mist into the inner cover 51, the gas mist is locally contacted to regions of the living body easily absorbing the gas mist, or to such regions especially absorbing the gas mist. At this time, for safety, the control device 60 allows for supplying or discharging the gas mist on the basis of the value of the manometer 71 such that the inside of the living body pressure bathing cover 50 is not brought above the predetermined pressure value.

The gas mists within the inner cover 51 and the outer cover 55 are discharged (Step S12). In the present embodiment, the gas mist is discharged outside from a gas mist discharge port (not shown) of the outer cover 55 or from the stopper 57.

Next, the gas mist is supplied from the gas mist generator 30 into the inner cover 51 and the outer cover 55 for a fixed time (Step S13). In this embodiment, similarly to Step S11, the gas mist is also supplied into the outer cover 55 via the inner cover 51. At this time, the control device 60 is controlled from the measured values of the manometer 71, such that air pressure in the inner cover 51 and the outer cover 55 is brought in the fixed range (more preferably, 1.01 to 2.5 air pressure). For safety, the control device 60 allows for supplying or discharging the gas mist gas on the basis of the value of the manometer 71, such that the inside of the living body pressure bathing cover 50 is not brought above the predetermined pressure value.

If stopping supply of the gas mist after maintaining the condition of Step S13, the gas mist gets away bit by bit from the inside of the outer cover 55 effected with pressure. Further, due to the body temperature, the temperature within the living body pressure bathing cover 50 heightens. Then, the operation again returns to Step S11. By repeating the above steps at plural turns (preferably, three turns), with respect to the skin and mucous membrane of the living body, sweating by temperature-rise in the cover and repeating the turn of the cutaneous absorption by suppressing evaporation of the gas mist, the gas mist can be absorbed at high efficiency.

By the way, in case the sealing property of the outer cover 55 is high or if necessary, it is sufficient to discharge the gas mist in the outer cover 55 and the inner cover 51 after Step S13.

The above explanation has been made to the example of the man's forearm as the region to be carried out with the gas mist pressure bathing, but the present invention can be applied to various regions of the living body. In such cases, the living body pressure bathing cover 50 meeting an object region is employed for taking the optimum gas mist pressure bathing.

FIGS. 11A to 11D show examples of various shapes of the living body pressure bathing cover 50.

Figure 11A:
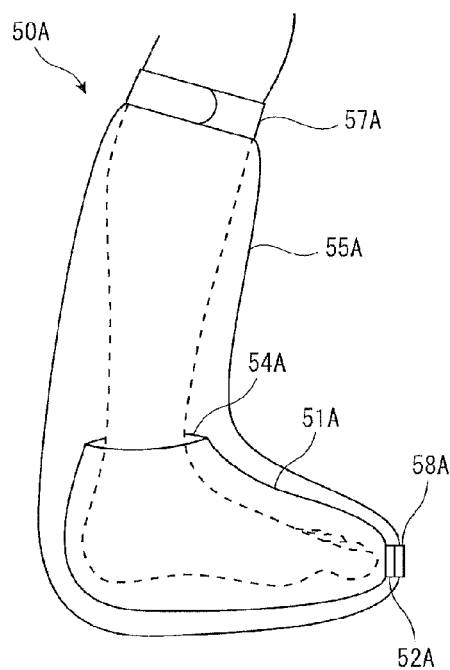

FIG. 11A is a living body pressure bathing cover 50A for a lower extremity (below the knee) of the human body. This living body pressure bathing cover 50A is composed of an inner cover 51A covering the whole of the foot and knee, and an outer cover 55A covering the part below the knee and the inner cover 51A. The inner cover 51A has a supply port 52A connecting to the gas mist supply pipe 41 for introducing inside the gas mist. The inner cover 51A is an opening 54A at an end. The outer cover 55A has a stopper 57A and a connection part 58A. The stopper 57A enabling to attach to and detach from the living body and avoiding leakage of the gas mist sealed inside, and the connection part 58A connecting the inner cover 51A to the gas mist supply pipe 41 while sealing the inside of the outer cover 55A by connecting the supply port 52A of the inner cover 51A and the gas mist supply pipe 41.

Figure 11B:
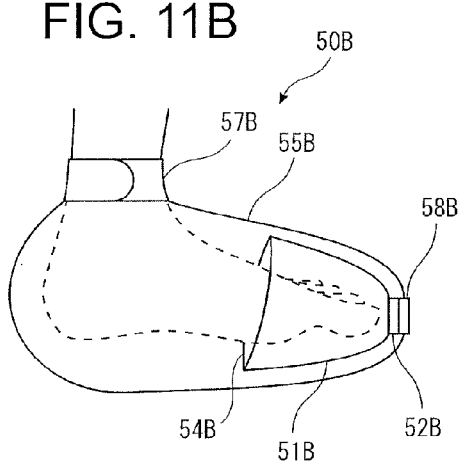

FIG. 11B is a living body pressure bathing cover 50B for a foot part of the human body. This living body pressure bathing cover 50B is composed of an inner cover 51B covering the foot toes, and an outer cover 55B covering the foot part and the inner cover 51B. The inner cover 51B has a supply port 52B connecting to the gas mist supply pipe 41 for introducing the gas mist inside. The inner cover 51B is an opening 54B at an end. The outer cover 55B has a stopper 57B and a connection part 58B, the stopper 57B enabling to attach to and detach from the living body and avoiding leakage of the gas mist sealed inside, and the connection part 58B connecting the inner cover 51B to the gas mist supply pipe 41 while sealing the inside of the outer cover 55B by connecting the supply port 52B of the inner cover 51B and the gas mist supply pipe 41.

Figure 11C:
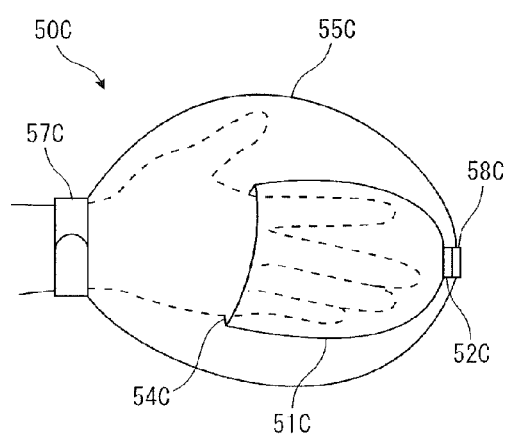

FIG. 11C is a living body pressure bathing cover 50C for a hand part of the human body. This living body pressure bathing cover 50C is composed of an inner cover 51C covering the hand fingers, and an outer cover 55C covering the hand part and the inner cover 51C. The inner cover 51C has a supply port 52C connecting to the gas mist supply pipe 41 for introducing the gas mist inside. The inner cover 51C is an opening 54C at an end. The outer cover 55C has a stopper 57C and a connection part 58C, the stopper 57C enabling to attach to and detach from the living body and avoiding leakage of the gas mist sealed inside, and the connection part 58C connecting the inner cover 51C to the gas mist supply pipe 41 while sealing the inside of the outer cover 55C by connecting the supply port 52C of the inner cover 51C and the gas mist supply pipe 41.

Figure 11D:
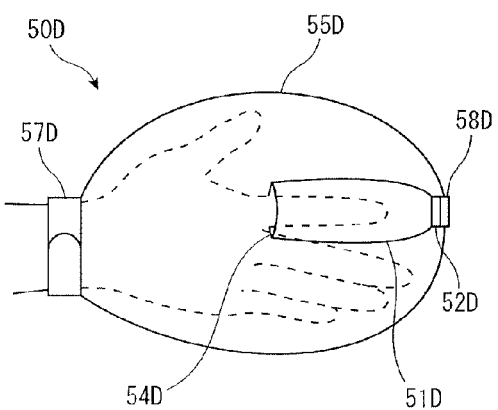

FIG. 11D is also a living body pressure bathing cover 50D for a hand part of the human body. This living body pressure bathing cover 50D is composed of an inner cover 51D covering the forefinger, and an outer cover 55D covering the hand part and the inner cover 51D. The inner cover 51D has a supply port 52D connecting to the gas mist supply pipe 41 for introducing the gas mist inside. The inner cover 51D is an opening 54D at an end. The outer cover 55D has a stopper 57D and a connection part 58D, the stopper 57D enabling to attach to and detach from the living body and avoiding leakage of the gas mist sealed inside, and the connection part 58D connecting the inner cover 51D to the gas mist supply pipe 41 while sealing the inside of the outer cover 55D by connecting the supply port 52D of the inner cover 51D and the gas mist supply pipe 41.

Second Embodiment

The above explanation has been made to the living body pressure bathing cover 50 where the inner cover 51 is opened by the opening 54, but the inner cover may be left as the inside being closed. The following explanation will be made to a living body pressure bathing cover 150 closed at the inner cover, referring to FIG. 12. Since the structure of the gas mist pressure bathing system is the same as the first embodiment excepting the living body pressure bathing cover 150, illustration and explanation thereof will be omitted.

The living body pressure bathing cover 150 is a cover which is such a cover for covering the skin and mucous membrane of the living body (in FIG. 12, as the example, a forearm of the human body) and forming a space for sealing the gas mist. The living body pressure bathing cover 150 is composed of a first cover (an inner cover) 151 positioned inside and a second cover (an outer cover) 155 positioned outside to cover the whole of the first cover 151 and enable to substantially seal. The living body pressure bathing cover 150 is preferably composed of pressure resistant, non-air permeable and non-moisture permeable materials, for example, the natural rubber, silicone rubber, polyethylene, polypropylene, poly-vinylidene, poly styrene, polyvinyl acetate, polyvinyl chloride, poly amide resin, polytetrafluoroethylene.

The inner cover 151 is a substantially bag-shaped cover for covering locally regions of the living body being high at absorption rate of the gas mist, and at the same time, functions as a heat insulating cover. Therefore, the inner cover 151 is suitably composed with a heat insulating material. By attaching this inner cover 151, it is possible to avoid evaporation of the gas mist supplied during taking the gas mist pressure bathing. The inner cover 151 is attached to such regions of the living body having many sweat glands and easily sweating as the palm or sole.

The inner cover 151 is connected to the gas mist supply pipe 41 and has a supply port 152 for introducing the gas mist into the inside. This supply port 152 is has a check valve for preventing back flows of the gas mist, though not showing. At an opening part of the inner cover 151, a stopper 153 is furnished for enabling to attach to and detach from the human body as well as for avoid leakage of the gas mist sealed inside. The stopper 153 is sufficiently composed of an elastic face fastener, string or rubber.

The stopper 153 of the inner cover 151 may be strongly attached to the human body to such a degree of enabling to seal the inside of the inner cover 151, or lightly engaged with a rubber or the like. Further, not showing, the inner cover 151 is suitably provided with a gas mist discharge port for discharging the gas mist from the inside of the cover, and with a valve for controlling pressure of the inside of the cover. Especially, a safety valve (escape valve) is desirably furnished for automatically opening the valve when the inside of the inner cover 151 comes above a fixed pressure value.

The outer cover 155 is larger than the inner cover 151, can cover wholly the skin and mucous membrane of the living body and the inner cover 151, and is formed almost as a bag. The outer cover 155 is connected to the gas mist supply pipe 41 and has a supply port 156 for introducing the gas mist into the inside thereof. This supply port 156 is provided with the check valve for avoiding back flows of the gas mist, though not showing. At an opening of the outer cover 155, a stopper 157 is furnished for enabling to attach to and detach from the living body and at the same time for avoiding leaking the gas mist sealed inside. The stopper 157 is suitably composed of, e.g., the face fastener of stretching property, or may have a string, rubber or their combination. Further, since the outer cover 155 necessitates a sealing property, the inside of the stopper 157 may be disposed with a material adhesive to the skin of the living body. This adhesive material is preferably, for example, a visco-elastic gel made of polyurethane or silicone rubber. Further this adhesive material is detachably used and exchangeable each time or if viscosity becomes weak.

Further, the outer cover 155 is provided with a connection part 158 for connecting a supply port 152 of the inner cover 151 and for connecting the inner cover 151 and the gas mist supply pipe 41 as closing the inside of the outer cover 155. Not showing, the outer cover 155 is suitably provided with a gas mist discharge port for discharging the gas mist from the inside of the cover, or with a valve for controlling pressure of the inside of the cover. Pressure within the cover may be controlled manually, but automatic performance is desirable by a control device 60 together with supply control of the gas mist based on measuring values of the manometer 71. The safety valve (escape valve) is desirably furnished for automatically opening the valve when the inside of the outer cover 155 comes above a fixed pressure value.

There has been shown such a structure, as an example, having the connection part 158 for connecting the supply port 152 of the inner cover 151, but if being able to supply the gas mist to the inner cover 151 as sealing the inside of the outer cover 155, any forms may be applied.

Figure 12:
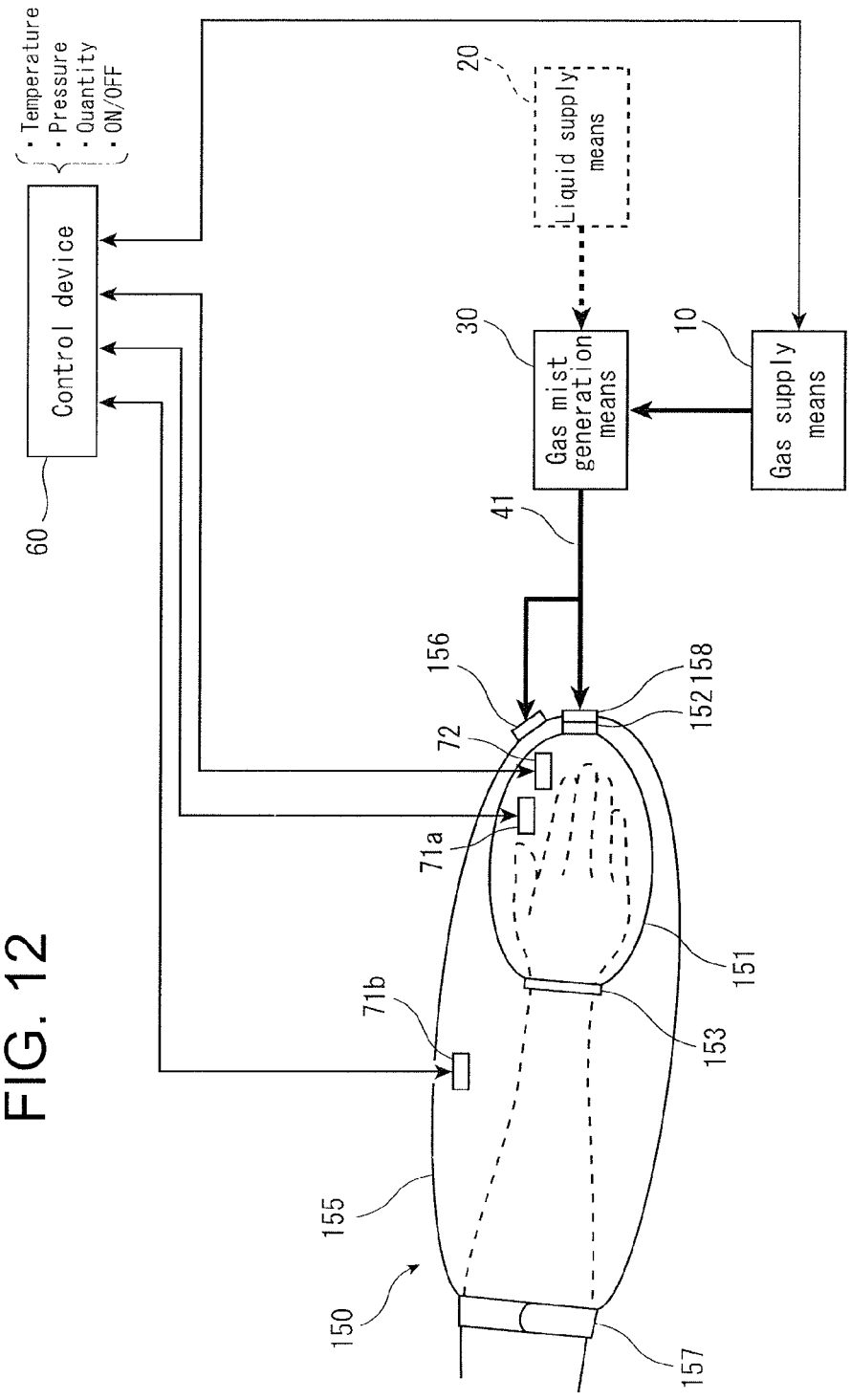

In the case of the living body pressure bathing cover 150 of the present embodiment, since the inner cover 151 and the outer cover 155 are independently structured respectively, it is preferable to furnish the respective manometers 71a, 71b to both covers 151, 155 as showing in FIG. 12. The temperature gage 72 may be furnished to the inner cover 151 only or to both of the inner cover 151 and outer cover 155.

Figure 13:
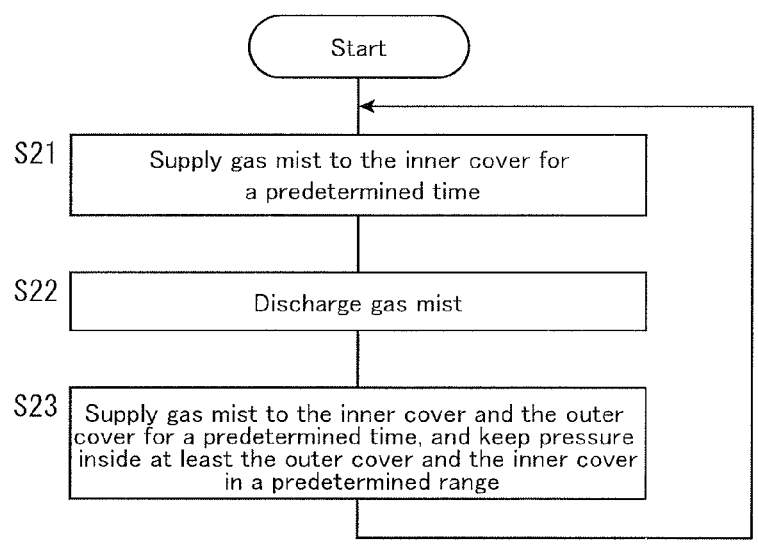

Following explanations will be made with FIG. 13 to the gas mist pressure bathing method using the gas mist pressure bathing system having the living body pressure bathing cover 150 of the present embodiment.

At first, as a preparatory step, the gas mist generator 30 is brought to under a usable condition as manners of opening the sealed gas mist generator 30 and connecting to the gas supply means 10. As to the living body pressure bathing cover 150, the inner cover 151 is attached to an optional part of the living body, and subsequently, the outer cover 155 is attached to cover the whole of the inner cover 151 for securing to the living body to seal the inside.

Gas supply is started from the gas supply means 10 into the gas mist generator 30 to generate the gas mist and supply it into the inner cover 151 for a predetermined time (Step S21). By supplying the gas mist into the inner cover 151, the gas mist is locally contacted to regions of the living body easily absorbing the gas mist or to such regions especially absorbing the gas mist. At this time, for safety, the control device 60 allows for supplying or discharging the gas mist on the basis of the value of the manometer 71a, such that the inside of the living body pressure bathing cover 151 is not brought above the predetermined pressure value.

Next, the gas mist within the inner cover 151 is discharged (Step S22). In this embodiment, the gas mist is once discharged into the outer cover 155 from a gas mist discharge port (not shown) of the inner cover 151 or from the stopper 153, and after then, the gas mist is discharged into the outer cover 155 from a gas mist discharge port (not shown) of the outer cover 155 or from the stopper 157. Otherwise, it is enough to only discharge the gas mist within the inner cover 151 into the outer cover 155.

The gas mist is supplied from the gas mist generator 30 into the inner cover 151 and the outer cover 155 through supply ports 152 and 156 for a fixed time (Step S23). At this time, the control device 60 is controlled from the measured values of the manometers 71a, 71b, such that air pressure in the inner cover 151 and the outer cover 155 is brought to in the fixed range (preferably, 1.01 to 2.5 air pressure). For safety, the control device 60 allows for supplying or discharging the gas mist on the basis of the values of the manometers 71a, 71b such that the inside of the living body pressure bathing cover 150 is not brought above the predetermined pressure value.

The above explanation has been made to the example of the man's forearm as the region to be carried out with the gas mist pressure bathing, and FIGS. 14A to 14D show examples of various shapes of the living body pressure bathing cover 150.

Figure 14A:
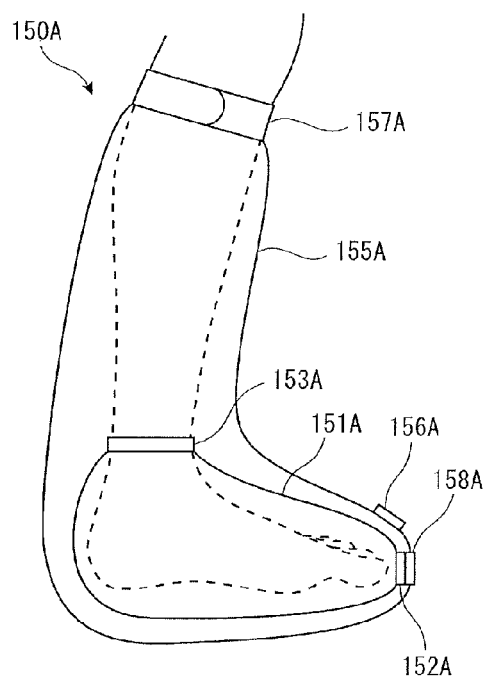

FIG. 14A is a living body pressure bathing cover 150A for a lower extremity (below the knee) of the human body. This living body pressure bathing cover 150A is composed of an inner cover 151A covering the whole of the foot and knee, and an outer cover 155A covering the part below the knee and the inner cover 151A. The inner cover 151A has a supply port 152A connecting to the gas mist supply pipe 41 for introducing inside the gas mist. Further, the inner cover 151A has a stopper 153A enabling to attach to and detach from the living body and avoiding leakage of the gas mist sealed inside. The outer cover 155A has a supply port 156A connecting to the gas mist supply pipe 41 for introducing the gas mist into the inside. The outer cover 155A has a stopper 157A and a connection part 158A, the stopper 157A enabling to attach to and detach from the living body and avoiding leakage of the gas mist sealed inside, and the connection part 58A connecting the inner cover 51A to the gas mist supply pipe 41 while sealing the inside of the outer cover 155A by connecting the supply port 152A of the inner cover 151A and the gas mist supply pipe 41.

Figure 14B:
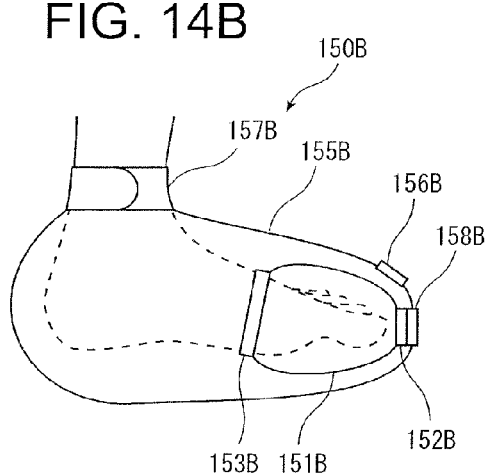

FIG. 14B is a living body pressure bathing cover 150R for a foot part of the human body. This living body pressure bathing cover 150B is composed of an inner cover 151B covering the foot toes and an outer cover 155B covering the foot part and the inner cover 151B. The inner cover 151B has a supply port 152B connecting to the gas mist supply pipe 41 for introducing inside the gas mist. The inner cover 151B is provided with a stopper 153B at its opening enabling to attach to and detach from the living body and avoiding leakage of the gas mist sealed inside. The outer cover 155B is provided with a supply port 156B connecting to the gas mist supply pipe 41 for introducing the gas mist inside. The outer cover 155B is provided with a stopper 157B and a connection part 158B, the stopper 157B enabling to attach to and detach from the living body and avoiding leakage of the gas mist sealed inside and the connection part 158B connecting the inner cover 151B to the gas mist supply pipe 41 while sealing the inside of the outer cover 155B by connecting the supply port 152B of the inner cover 151B and the gas mist supply pipe 41.

Figure 14C:
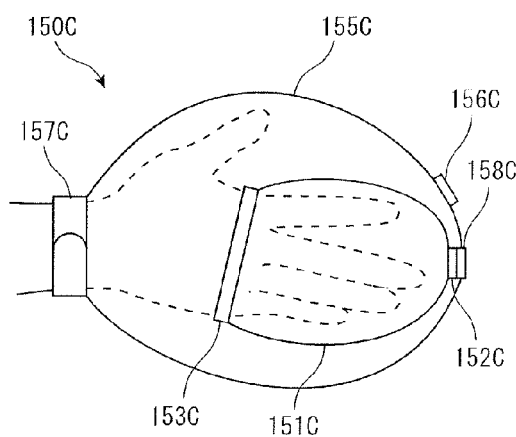

FIG. 14C is a living body pressure bathing cover 150C for a hand part of the human body. This living body pressure bathing cover 150C is composed of an inner cover 151C covering the hand fingers, and an outer cover 155C covering the hand part and the inner cover 151C. The inner cover 151C has a supply port 152C connecting to the gas mist supply pipe 41 for introducing the gas mist inside. The inner cover 151C is provided with a stopper 157C at its opening for enabling to attach to and detach from the living body and avoiding leakage of the gas mist sealed inside. The outer cover 155C has a supply port 156C connecting to the gas mist connection pipe 41 for introducing the gas mist gas inside. The outer cover 155C is provided with a stopper 157C and a connection part 158C, the stopper 157C enabling to attach to and detach from the living organ, and the connection part 158C connecting the inner cover 151B to the gas mist supply pipe 41 while sealing the inside of the outer cover 155C by connecting the supply port 152C of the inner cover 151C and the gas mist supply pipe 41.

Figure 14D:
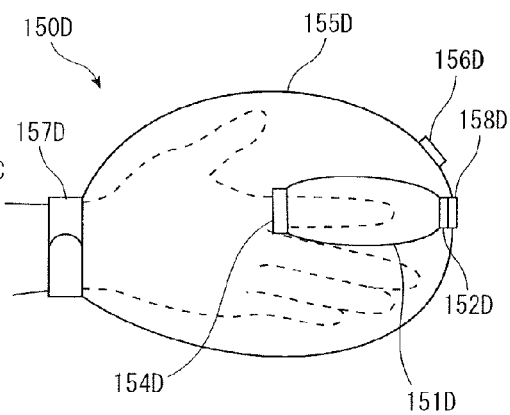

FIG. 14D is also a living body pressure bathing cover 150D for a hand part of the human body. This living body pressure bathing cover 150D is composed of an inner cover 151D covering the forefinger, and an outer cover 155D covering the hand part and the inner cover 151D. The inner cover 151D has a supply port 152D connecting to the gas mist supply pipe 41 for introducing the gas mist inside. The inner cover 151D is provided with a stopper 153D at its opening enabling to attach to and detach from the living body and avoiding leakage of the gas mist sealed inside. The outer cover 155D is provided with a supply port 156D connecting to the gas mist supply pipe 41 for introducing the gas mist gas inside. The outer cover 155D is provided with a stopper 157D and a connection part 158D, the stopper 157D enabling to attach to and detach from the living body and avoiding leakage of the gas mist sealed inside, and the connection part 158D connecting the inner cover 151D to the gas mist supply pipe 41 while sealing the inside of the outer cover 155D by connecting the supply port 152B of the inner cover 151D and the gas mist supply pipe 41.

The living body pressure bathing covers 50, 150 mentioned in the first and second embodiments can be applied to various regions of the living body other than the examples illustrated up to now, and therefore, many other modifications are available. In particular, since the present invention can be practiced not only to the human bodies but also to whole of animals, shapes meeting to using objects and using regions are employed. In sum, if the shapes can cover the skin and mucous membrane of the living bodies and can form spaces for sealing the gas mist inside, any shapes can be employed.

Third Embodiment

FIG. 15 is the whole schematic view of the gas mist pressure bathing system depending on the third embodiment of the present invention. This embodiment will explain the gas mist pressure bathing system having further an electric charge giving means for charging generated mist. As to the same parts as those of the first embodiment Shown in FIG. 2, the same signs will be given to and detailed explanation will be omitted.

As showing in FIG. 15, the gas mist pressure bathing system disposes an electrode 82 in the vicinity of the gas mist port 31 of the gas mist generator 30. The electrode 82 is connected to a power supply device 81, and sets a voltage value and controls ON/OFF by the control device 60.

The electrode 82 gives an electric charge (minus electric charge is desirous) when the gas mist generated by the gas mist generator 30 is discharged. The mist is made thereby electrically charged and can heighten adherence to a charged material. That is, if heightening adherence to the skin and mucous membrane of the living body, an effect of improving absorption of gas by the gas mist pressure bathing is further heightened, and in case the above mentioned medicines are contained in the gas mist, it is made possible to more accelerate penetration into the skin and mucous membrane.

In the above mentioned respective embodiments, if a simple means like the cartridge system gas bomb is used for the gas supply means 10, it is possible to use the gas supply means 10 and the gas mist generator 30 (more preferably, the control device 60) under a compact condition of containing them in the case 90 as showing in FIG. 16. Herein, the gas supply means 10 has a regulator 11. In FIGS. 17A to 17C, examples of using conditions are shown. As showing in FIGS. 17A to 17C, the cases 90 have stands 91, 92 or a hook 93 to stand upright, or the case 90 is suspended from a wall, so that the gas mist generator 30 is used as standing as possible. By such manners, the liquefied gas mist is easily recovered.

In the gas mist pressure bathing, the gas mist is contacted to the skin and mucous membrane of the living body at higher pressure than fixed by the living body pressure bathing covers 50, 150, and such pressurization is heightened in effect by pulse-shaped performance at predetermined intervals. Therefore, by supplying gas intermittently from the gas supply means 10 into the gas mist generator 30, the control device 60 may supply the gas mist into the living body pressure bathing covers 50, 150. Then, the effect is heightened by synchronizing rhythm of supplying to pulsation.

Having structured as above, according to the gas mist pressure bathing method and the gas mist pressure bathing system of the present invention, the gas mist pressure bathing effect can be improved by contacting the gas mist to the skin and mucous membrane of the living body sweated and easily absorbing the gas mist under the optimum pressurized condition.

The above references have explained the embodiments of the invention, but are not limited thereto, and so far as not deviating from the subject matter of the invention, various kinds of embodiments are, of course, available.

INDUSTRIAL APPLICABILITY

The invention relates to the gas mist pressure bathing method and the gas mist pressure bathing system for improving absorption efficiency of gas mist into the skin or the mucous membrane of the living body, in which the gas mist is prepared by pulverizing and dissolving oxygen or carbon dioxide, or mixed gas of oxygen and carbon dioxide and the liquid, and the gas mist is caused to directly contact the skin and mucous membrane of the living body at pressure of not less than the fixed value, and has industrial applicability.

EXPLANATION OF THE REFERENCE NUMERALS AND SIGNS

10: Gas supply means
10A: gas bomb
11: regulator
20: liquid supply means
30, 130, 230, 230', 330, 430: gas mist generators
31, 133, 234, 239, 337, 433: gas mist discharge port
41: gas mist supply pipe
41A: cornice shaped pipe
42: groove
50, 50A, 50B, 50C, 50D, 150, 150A, 150B, 150C, 150D: living body pressure bathing cover
51, 51A, 51B, 51C, 51D, 151, 151A, 151B, 151C, 151D: first cover (inner covers),
52, 52A, 52B, 52C, 52D, 152, 152A, 152B, 152C, 152D, 156, 156A, 156B, 1560, 156D: supply port
54, 54A, 54B, 54C, 54D: opening
55, 55A, 55B, 55C, 55D, 155, 155A, 155B, 155C, 155D: second covers (outer covers)
57, 57A, 57B, 57C, 57D, 153, 153A, 153B, 153C, 153D, 157, 157A, 157B, 157C, 157D: stopper
58, 58A, 58B, 58C, 58D, 158, 158A, 158B, 158C, 158D: connection part
60: control device
71, 71a, 71b: manometer
72: temperature gage
81: power supply device
82: electrode
90: case
91, 92: stand
93: hook
131, 231, 235, 331B, 431: liquid storage
132: gas introduction part
132A: connection part
132B: fine pores
134: cap
232, 236, 432A: gas supply port
233, 237: supersonic vibrator
238: vibration transmitting cistern
331: storage
331A: gas mist storage
332: nozzle
332A: front end open of the nozzle
333: liquid suction pipe
334: baffle
335: shield plate
336: liquid suction pipe-forming member
336A: front end of the liquid suction pipe-forming member
432: liquid nozzle
432B: liquid supply port
434: liquid discharge part
435: liquid circulation path

The invention claimed is:

1. A gas mist pressure bathing system producing a gas mist with a liquid and gas of carbon dioxide or oxygen, or a mixed gas of carbon dioxide and oxygen, the liquid and the gas or the mixed gas being pulverized and dissolved each other, and contacting the gas mist with a skin or a mucous membrane of a living body, the gas mist pressure bathing system comprising:
a gas supply source supplying the gas or the mixed gas,
a gas mist generator having a liquid storage for generating the gas mist with the gas or the mixed gas supplied from the gas supply source and the liquid stored in the liquid storage, and
a living body covering member which is a cover covering the skin and the mucous membrane of the living body and formed with a space for sealing inside the gas mist supplied from the gas mist generator, having a first cover placed inside and a second cover placed outside of the first cover and substantially sealing an inside of the first cover,
wherein
the first cover has a supply port introducing the gas mist in the first cover at a longitudinal end thereof, and an opening at another longitudinal end thereof,
the second cover has a connection part connected with the supply port at a longitudinal end thereof, and connecting the first cover and the gas mist generator while closing an inside of the second cover,
a longitudinal length of the first cover is shorter than a longitudinal length of the second cover, and
when the gas mist is supplied to the living body covering member from the gas mist generator, the gas mist contacts a covering region of the first cover and subsequently the gas mist is introduced into the second cover through the opening.

2. The gas mist pressure bathing system as set forth in claim 1, further comprising a liquid supply part supplying the liquid to the gas mist generator.

3. The gas mist pressure bathing system as set forth in claim 2, further comprising
manometers measuring pressure within the first cover and the second cover, and
a control device controlling air pressure within the first and second covers to be within predetermined values based on values measured by the manometers.

4. The gas mist pressure bathing system as set forth in claim 1, further comprising
a control device, and
one or plural sensors for measuring temperature, concentration of oxygen, concentration of carbon dioxide, or moisture within the first cover or second cover,
wherein the control device controls environments in the first cover or the second cover to be within predetermined values, based on values measured by the one or plural sensors.

5. The gas mist pressure bathing system as set forth in claim 4, wherein the first cover has a shape of releasing the inside by the opening.

6. The gas mist pressure bathing system as set forth in claim 5, wherein the first cover has a shape of closing the inside.

7. The gas mist pressure bathing system as set forth in claim 4, wherein the control device controls an amount of supply of the gas or the mixed gas such that the gas or the mixed gas is intermittently supplied from the gas supply source into the gas mist generator to effect interval pressurization on the living body covering member.

8. The gas mist pressure bathing system as set forth in claim 4, wherein the control device stops gas supply from the gas supply source when pressure value within the living body covering member exceeds a predetermined value.

9. The gas mist pressure bathing system as set forth in claim 1, wherein the first cover includes a hand palm or a foot sole in the covering region.

10. The gas mist pressure bathing system as set forth in claim 1, wherein the liquid is any one or plural combination of water, ionic water, ozone water, physiological salt solution, purified water, or sterilized and purified water.

11. The gas mist pressure bathing system as set forth in claim 10, wherein the liquid is any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, citric acid, ethanol, chlorhexidine gluconate, amphoteric surface active agent, benzalkonium chloride, alkyl diamino etherglycine acetate, sodium hypochlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

12. The gas mist pressure bathing system as set forth in claim 1, wherein a size of the gas mist supplied from the gas mist generator into the living body covering member is not larger than 10 μm.

13. The gas mist pressure bathing system as set forth in claim 1, wherein an electrode is provided for giving an electric charge to the gas mist supplied by the gas mist generator.

14. The gas mist pressure bathing system as set forth in claim 13, wherein the electric charge is minus.

15. The gas mist pressure bathing system as set forth in claim 1, wherein the gas mist generator has a gas mist supply pipe for supplying the gas mist into the living body covering member, and the gas mist supply pipe has a cornice shaped pipe over a whole or at one part of the gas mist supply pipe.

16. The gas mist pressure bathing system as set forth in claim 15, wherein the cornice shaped pipe is formed inside with a groove in a shaft direction of the pipe.

17. The gas mist pressure bathing system as set forth in claim 1, wherein the first cover is a heat insulating cover.

\* \* \* \* \*